US010436767B2

United States Patent
Bellotti et al.

(10) Patent No.: US 10,436,767 B2
(45) Date of Patent: *Oct. 8, 2019

(54) APPARATUS AND METHOD FOR NON-DESTRUCTIVE TESTING OF CONCRETE

(71) Applicant: NLA Diagnostics LLC, Charlotte, NC (US)

(72) Inventors: Aldo Bellotti, Charlotte, NC (US); Ralph N. Strayhorn, IV, Charlotte, NC (US)

(73) Assignee: NLA Diagnostics LLC, Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/948,963

(22) Filed: Apr. 9, 2018

(65) Prior Publication Data

US 2018/0231519 A1    Aug. 16, 2018

Related U.S. Application Data

(63) Continuation of application No. 14/698,603, filed on Apr. 28, 2015, now Pat. No. 9,939,420.

(Continued)

(51) Int. Cl.
*G01N 29/07*  (2006.01)
*G01N 29/34*  (2006.01)
*G01N 33/38*  (2006.01)

(52) U.S. Cl.
CPC ............ *G01N 33/383* (2013.01); *G01N 29/07* (2013.01); *G01N 29/348* (2013.01);
(Continued)

(58) Field of Classification Search
CPC ..... G01N 29/348; G01N 33/383; G01N 29/07; G01N 2291/011; G01N 2291/0232; G01N 2291/0422; G01N 2291/02827
(Continued)

(56) References Cited

U.S. PATENT DOCUMENTS 3,106,838 A * 10/1963 Crooks .................. G01M 7/08
                                                                        73/582
3,580,056 A *  5/1971 Warner .................. G01H 13/00
                                                                        324/226
(Continued)

FOREIGN PATENT DOCUMENTS

EP    1892525       2/2008
JP    2006029946    4/1995
WO    2010150109   12/2010

OTHER PUBLICATIONS

International Atomic Energy Agency. "Guidebook on Non-Destructive Testing of Concrete Structures." Training Course Series No. 17, Vienna, 2002.
(Continued)

*Primary Examiner* — Jacques M Saint Surin
(74) *Attorney, Agent, or Firm* — Nelson Mullins Riley & Scarborough LLP

(57) ABSTRACT

A device and method for determining characteristics of a concrete sample includes the use of multiple transducers. The transducers may couple to the concrete surface so that they can impart or receive mechanical waves from the sample. An area within a plane in the concrete sample is bounded by a collective extent of mechanical waves that pass through the plane and has a dimension at least as long as a distance between reinforcing bars in the concrete.

22 Claims, 14 Drawing Sheets

Related U.S. Application Data

(60) Provisional application No. 61/986,029, filed on Apr. 29, 2014.

(52) U.S. Cl.
CPC .................. *G01N 2291/011* (2013.01); *G01N 2291/0232* (2013.01); *G01N 2291/02827* (2013.01); *G01N 2291/0422* (2013.01)

(58) Field of Classification Search
USPC .......................................................... 73/597
See application file for complete search history.

(56) References Cited

U.S. PATENT DOCUMENTS

| | | | |
|---|---|---|---|
| 3,616,682 A * | 11/1971 | Mcmaster et al. | B06B 1/0622 310/326 |
| 3,967,498 A * | 7/1976 | Pezzillo | G01M 17/025 73/146 |
| 4,023,396 A | 5/1977 | Yakshin et al. | |
| 4,470,293 A | 9/1984 | Redmon | |
| 4,519,245 A | 5/1985 | Evans | |
| 4,615,209 A | 10/1986 | Change, Jr. | |
| 4,682,490 A | 7/1987 | Adelman et al. | |
| 4,799,375 A | 1/1989 | Lally | |
| 4,918,988 A | 4/1990 | Ebihara et al. | |
| 5,003,811 A | 4/1991 | Shannon et al. | |
| 5,025,655 A | 6/1991 | Umemura et al. | |
| 5,048,320 A | 9/1991 | Mitsuhashi et al. | |
| 5,122,993 A | 6/1992 | Hikita et al. | |
| 5,165,270 A | 11/1992 | Sansalone et al. | |
| 5,404,755 A | 4/1995 | Olson et al. | |
| 5,490,411 A | 2/1996 | Hogan | |
| 5,614,670 A | 3/1997 | Nazarian et al. | |
| 5,686,652 A | 11/1997 | Pfund | |
| 5,748,758 A | 5/1998 | Menasco, Jr. et al. | |
| 5,814,731 A | 9/1998 | Alexander et al. | |
| 6,026,686 A | 2/2000 | Hattori et al. | |
| 6,112,599 A | 9/2000 | Maki, Jr. | |
| 6,230,552 B1 * | 5/2001 | Abe | G01B 11/303 73/104 |
| 6,239,867 B1 | 5/2001 | Aggarwal | |
| 6,279,396 B1 * | 8/2001 | Imagawa | G01S 7/524 73/1.79 |
| 6,301,967 B1 | 10/2001 | Donskoy et al. | |
| 6,429,802 B1 | 8/2002 | Roberts | |
| 6,581,466 B1 | 6/2003 | Costley et al. | |
| 6,598,485 B1 | 7/2003 | Lin et al. | |
| 6,684,681 B1 | 2/2004 | Zombo | |
| 6,748,791 B1 | 6/2004 | Georgeson et al. | |
| 7,036,605 B2 | 5/2006 | Suzuki et al. | |
| 7,106,869 B2 | 9/2006 | Kanda et al. | |
| 7,121,136 B2 | 10/2006 | Tsujii et al. | |
| 7,367,236 B2 | 5/2008 | Georgeson et al. | |
| 7,412,870 B2 | 8/2008 | Brankov | |
| 7,516,646 B2 | 4/2009 | Makimoto et al. | |
| 7,668,667 B2 | 2/2010 | Robb et al. | |
| 7,900,498 B1 | 3/2011 | Ratcliffe | |
| 7,963,919 B2 | 6/2011 | Proulx et al. | |
| 8,079,265 B2 | 12/2011 | Brignac et al. | |
| 8,327,709 B2 | 12/2012 | Daraio et al. | |
| 8,490,493 B2 | 7/2013 | Milmann et al. | |
| 8,515,702 B2 | 8/2013 | Daw et al. | |
| 8,567,252 B2 | 10/2013 | Fisk | |
| 8,701,494 B1 | 4/2014 | Saxena et al. | |
| 8,996,319 B2 | 3/2015 | Cokonaj | |
| 9,939,420 B2 * | 4/2018 | Bellotti | G01N 33/383 |
| 2002/0183942 A1 | 12/2002 | Lafleur et al. | |
| 2002/0184950 A1 * | 12/2002 | Kepler | G01N 29/2418 73/594 |
| 2007/0034009 A1 | 2/2007 | Pado | |
| 2009/0043516 A1 | 2/2009 | Bao et al. | |
| 2009/0143681 A1 | 6/2009 | Jurvelin et al. | |
| 2010/0286527 A1 | 11/2010 | Cannon et al. | |
| 2010/0312496 A1 | 12/2010 | Armitage | |
| 2011/0179873 A1 * | 7/2011 | Schubert | G01N 29/07 73/597 |
| 2013/0060140 A1 | 3/2013 | Sinelnikov | |
| 2013/0073246 A1 | 3/2013 | Sprague | |
| 2013/0178915 A1 | 7/2013 | Radziemski et al. | |
| 2013/0250719 A1 | 9/2013 | Kollgaard et al. | |
| 2013/0276539 A1 | 10/2013 | Wagner et al. | |
| 2013/0286778 A1 | 10/2013 | Kisner et al. | |
| 2014/0056104 A1 | 2/2014 | Buechler et al. | |
| 2014/0260527 A1 * | 9/2014 | Mazzeo | G01N 29/045 73/12.05 |
| 2014/0311244 A1 | 10/2014 | Armitage | |
| 2017/0074830 A1 | 3/2017 | Bellotti et al. | |

OTHER PUBLICATIONS

Pristov, E., Dalton, W., Piscsalko, G., and Likins, G. "Comparison of Impact-Echo with Broadband Input to Determine Soncrete Thickness." Proc. NDE Conference on Civil Engineering, Aug., 2006, pp. 254-261.

Gibson, A. and Popovics, J.S., 2005 "Lamb Wave Basis for Impact-Echo Method Analysis," Journal of Engineering Mechanics (ASCE), vol. 131, No. 4, Apr., pp. 438-443.

ASTM C597-09, "Standard Test Method for Pulse Velocity Through Concrete.".

NDT Instruments: BondMaster 600, "BondMaster 600 Multimode Bond Tester.".

Malhotra, V.M., Carette, G.G., Carina, N.J., Naik, T.R., Henderson, G.D., Basheer, P.A.M., Long, A.E., Sivasundaram, V., Samarin, A., Lauer, K.R., Mitchell, T.M., Clemetia, G.G., Wiel, G.J., Mindess, S. "Handbook on Nondestructive Testing of Concrete." CRC Press. Jan. 2004.

ACI 318-11, "Building Code Requirements for Structural Concrete and Commentary." American Concrete Institute, Farmington Hills, MI. Aug. 2011.

Hartsuijker, C., Welleman, J., "Engineering Mechanics vol. 2." Springer, 2001. Chapters 1 and 9. ISBN 978-1-40 (e-book).

Army—Department of Defense solicitation—A12a-T013—Proposal Submission Instructions.

Nila Diagnostics, LLC Proposal to Department of Defense solicitation—A12a-1013.

Fifth Month Progress Report.

NILA Defender specifications sheet.

Carino, N. J. "The Impact-Echo Method: An Overview." National Institute of Standards and Technology, May 21, 2001.

Haroon, Muhammad, et al. "Implementation of Nonlinear Acoustic Techniques for Crack Detection in a Slender Beam Specimen." Proc. of SPIE vol. 6935, 2008 SPIE Digital Library.

Field Instruments for Nondestructive Evaluation of Concrete & Masonry. Impact-Echo Instruments, LLC, Aug. 2005.

Engholm, Marcus "A Narrowband Ultrasonic Spectroscopy Technique for the Inspection of Layered Structures." iniversitetstryckenet, Uppsala, Aug. 2006.

Olson Instruments: NDE 360 Nondestructive Testing Plattorm. www.olsoninstruments.com, Mar. 4, 2014.

Ageeva, Victoria, et al. "Integrative Solution for In-situ Ultrasonic Inspection of Aero-engine Blades Using Endoscopic 3heap Optical Transducers (CHOTs)." 5th International Symposium on NDT in Aerospace, Nov. 13-15, 2013, Singapore.

Standard Test Method for Pulse Velocity Through Concrete, ASTM Designation: C 597—83 (Reapproved 1991).

Standard Test Method for Measuring the P-Wave Speed and the Thickness of Concrete Plates Using the Impact-Echo Method, ASTM International Designation: C1383—04 (Reapproved 2010).

Zhu, Jinying. "Non-Contact NDT of Concrete Structures Using Air-Coupled Sensors." University of Illinois at Urbana-3hampaign, 2005.

Hoegh K., Khazanovich L., Yu H.T. "Ultrasonic Tomography Technique for Evaluation of Concrete Pavements." Transportation Research Record: Journal of the Transportation Research Board, No. 2232, pp. 85-94. 2011.

(56) References Cited

OTHER PUBLICATIONS

International Search Report and Written Opinion dated Aug. 5, 2015, for corresponding Application No. PCT/US15/28074.

* cited by examiner

| CLOCK μSEC | TOTAL SAMPLES | MAX μSEC | SAMPLING PERIOD μSEC | # SAMPLES | TIME μSEC | FREQ. CHANNELS # BINS | FREQ. INTERVAL Hz | MAX FREQ. kHz |
|---|---|---|---|---|---|---|---|---|
| 0.1 | 64000 | 6400 | 0.4 | 1024 | 410 | 512 | 2441 | 1250 |
|  |  |  | 2 |  | 2048 |  | 488 | 250 |
|  |  |  | 4 |  | 4096 |  | 244 | 125 |
|  |  |  | 6 |  | 6144 |  | 163 | 83 |
| 0.2 | 64000 | 12800 | 0.2 | 1024 | 205 | 512 | 4883 | 2500 |
|  |  |  | 0.8 |  | 819 |  | 1221 | 625 |
|  |  |  | 4 |  | 4096 |  | 244 | 125 |
|  |  |  | 8 |  | 8192 |  | 122 | 63 |
|  |  |  | 12 |  | 12288 |  | 81 | 42 |

FIG. 6

Mark rebar position

Remove unit from wall, and install protective cover.

Connect Broadband Transducer and Impact Hammer

After you press "Next"

Carry unit with shoulder strap

Press Transducer to wall and make an impact

—206

Next

© NLA Diagnostics

APPARATUS AND METHOD FOR NON-DESTRUCTIVE TESTING OF CONCRETE

The present application is a continuation of U.S. application Ser. No. 14/698,603, filed Apr. 28, 2015, now U.S. Pat. No. 9,939,420, which claims priority to U.S. provisional patent application Ser. No. 61/986,029, filed Apr. 29, 2014, entitled APPARATUS AND METHOD FOR NON-DESTRUCTIVE TESTING OF CONCRETE, the entire disclosure of each of which is hereby incorporated by reference herein.

This invention was made with government support under contract number W911NF-14-C-0010 awarded by the Department of Defense. The government has certain rights in the invention.

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright whatsoever.

BACKGROUND

The present invention relates to the use of mechanical waves in the non-destructive testing of concrete.

Methods and devices are known that utilize the propagation and reception of mechanical waves within the acoustic and ultrasonic frequency ranges for testing characteristics of concrete.

Ultrasonic pulse velocity (UPV) test methods utilize piezoelectric transducers on opposite or adjacent sides of a concrete sample to determine the velocity of an ultrasonic signal transmitted through the concrete from one transducer to the other. Because defects in the concrete, such as voids or delaminations, can affect ultrasonic mechanical wave speed through the sample, the amount of variation in the signal velocity as measurements are taken across a concrete sample can indicate the presence of such defects or the presence of material such as metal reinforcing bars (rebar). Further, the UPV test method can be used to determine compressive strength. As should be understood, compressive strength is an estimate of the maximum amount of force that can be applied normally to a surface of the concrete sample without crushing the concrete.

ASTM C 597 describes a standard test method for utilizing pulse velocity through concrete. In one example of such method, respective transducers are disposed on opposite or adjacent sides of a concrete sample, such as a wall. Each transducer includes a piezoelectric element, as should be understood in this art, but other transducer crystals can be used. An impedance matching material, which is used to decrease the impedance difference between the piezoelectric material and the concrete, is disposed between each transducer's piezoelectric element and the concrete surface, and a gel is disposed between the impedance matching material and the concrete to fill air gaps. A control system excites one of the two narrowband transducers to impart a pulse of ultrasonic longitudinal mechanical waves (primary waves, or "p-waves") into the concrete surface, at a frequency ranging from 50 kHz to 120 kHz. The pulse travels through the concrete and undergoes multiple reflections at occurrences of density variations within the concrete, for example due to delamination, air pockets, or rebar. A complex system of mechanical waves develops, including both p-waves and shear (or "s") waves, and propagates through the concrete. P-waves travel faster than s-waves, and where the transducers are disposed are opposite sides of the concrete sample, the p-wave therefore first reaches the piezoelectric receiving transducer, which in turn converts the p-wave into an electrical signal. The transit time ($T_P$) for the pulse to travel the known path length (L) is measured by the control system, and the longitudinal pulse velocity ($C_p$) is given by the following equation:

$$C_p = \frac{L}{T_p}$$

The accuracy of the velocity measured by this method is a function of the accuracy of the measured distance (L) between the transducers and the measured transit time ($T_P$). For the pulse velocity operational mode, the programmable data acquisition has a sampling period (h), or transit time resolution, e.g. of 0.1 microseconds using a 10 MHz clock.

Shear waves also reach the opposite side of the concrete wall, and using a pair of shear wave transducers similarly disposed on opposite or adjacent sides of the concrete as the p-wave transducers, the s-wave transit time ($T_S$) is similarly measured. As should be understood in this art, s-wave transducers are piezoelectric devices configured to mechanically react in response to shear waves, thereby producing an electrical signal when the transducer is affected by a shear wave. Given the path length (L), the shear velocity ($C_s$) is given by the following equation:

$$C_s = \frac{L}{T_s}$$

The p-wave velocity ($C_p$) and shear velocity ($C_s$) are correlated to the Young's modulus (E), Poisson's ratio (v), and density (ρ) of the material as determined by the following equations:

$$C_p = \sqrt{\frac{E(1-v)}{\rho(1-2v)(1+v)}}$$

$$C_s = \sqrt{\frac{E}{2\rho(1+v)}}$$

The p-wave modulus (M) is correlated to the p-wave velocity ($C_p$) and density (ρ) of the material as determined by the following equation:

$$M = \rho C_p^2$$

Using shear wave transducers, the shear modulus (G) can be correlated to shear velocity ($C_s$) and density (ρ) of the material as determined by the following equations:

$$G = \rho C_s^2$$

$$v = \frac{M-2G}{2M-2G} = \frac{C_p^2 - 2C_s^2}{2(C_p^2 - C_s^2)}$$

Thus, the Poisson's ratio (v) can be determined without knowing the concrete density by measuring the p-wave velocity ($C_p$) and shear velocity ($C_s$). Once the Poisson's ratio (ν) is known, the control system calculates the Young's modulus (E) from the above equation, where density (ρ) is known from empirical destructive (stress/strain) testing. For conventional concrete from 200 psi to 3,000 psi, the compressive strength (σ) can be calculated from the following equation:

$$E = 0.043 \rho^{1.5} \sqrt{\sigma}$$

Where density (ρ) is in units of kg/m³, and Young's modulus (E) and compressive strength (σ) are in MPa, the above equation is applicable to twenty-eight day compressive strength, and the following adaption of the American Concrete Institute (ACI) equation can be used, with the value of the proportionality constant (k) determined by curve fitting experimental data:

$$E = k\sqrt{\sigma}$$

The American Concrete Institute (ACI) Committee 318 recommends a model to predict the modulus of elasticity for a wide range of concrete compressive strengths from 200 psi to 3,000 psi, although overestimating the modulus of elasticity for compressive strength over 6,000 psi [ACI 318-11].

$$E = 0.043 \rho^{1.5} \sqrt{\sigma}$$

where:
E=modulus of elasticity in MPa
ρ=density in kg/m³
σ=compressive strength in MPa $$E = 4.38 \rho^{1.5} \sigma^{0.75}$$

where:
E=modulus of elasticity in psi (English)
ρ=density in pcf or lb/ft³ (English)
σ=compressive strength in psi (English)

The ACI Committee 363 recommends a model for higher strength concretes ranging from 3,000 psi to 12,000 psi [ACI 363R-92].

$$E = 3320\sqrt{\sigma} + 6900$$

where:
E=modulus of elasticity in MPa
ρ=density in kg/m³=2323 kg/m³
σ=compressive strength in MPa $$E = (40000\sqrt{\sigma} + 1.0 \times 10^6)(\rho/145)^{1.5}$$

where:
E=modulus of elasticity in psi (English)
ρ=density in pcf or lb/ft³ (English)=145 lb./ft³
σ=compressive strength in psi (English)

The Architectural Institute of Japan (AIJ) recommends an equation to predict the modulus of elasticity for high-strength concretes ranging from 2,900 psi to 23,200 psi [Tomosawa, et al 1990]. The AIJ equation expresses the modulus of elasticity (E) as a function of compressive strength (σ), and density (ρ):

$$E = k1486 \sigma^{1/3} \rho^2$$

where:
E=modulus of elasticity in MPa
ρ=density in kg/m³
σ=compressive strength in MPa
k=$k_1 k_2$
$k_1$=correction factor corresponding to coarse aggregates
$k_2$=correction factor corresponding to mineral admixtures Compressive strength may also be determined by acoustic attenuation or relative amplitude, which measures the attenuation of an acoustic wave by observing the ratio of the wave amplitudes. As ultrasonic waves pass through materials, attenuation is caused by beam divergence (distance effect), absorption (heat dissipation), and scattering. Scattering is the only form of attenuation affected by the characteristics of the materials through which the waves pass, as well as the degree of inhomogeneity and frequency of the transducer. Attenuation caused by scattering ($\alpha_S$) is given by:

$$\alpha_s \propto \begin{cases} 1/D & \text{for diffusion range } \lambda \leq D \\ Df^2 & \text{for stochastic range } \lambda \approx D \\ D^3 f^4 & \text{for Raleigh range } \lambda \gg D \end{cases}$$

where f is the wave frequency, λ is the wavelength, and D is the average inhomogeneity in concrete. D may also be the void or aggregate size. For λ much greater than D, concrete strength is related exponentially with the wave attenuation.

Porosity is the main factor influencing strength of a brittle material such as concrete. Several models that relate strength to porosity exist, but the most common is the exponential model:

$$K = K_0 e^{-kP}$$

where $K_0$ is the strength at zero porosity, P is the fractional porosity, and k is a constant that depends on the system being studied.

Techniques for determining ultrasonic attenuation include placement of receiving and transmitting transducers on opposite or adjacent sides of a concrete sample. Typically, the use of adjacent sides is not possible because the amplitude of the pressure and the torsion waves are difficult to determine. However, when thickness of the structure is known, it may be possible to utilize an impulse reflected off of the opposing surface of the concrete sample, assuming a sufficiently high input signal.

When porosity is not known, the relative amplitude (β) can be correlated to the fractional porosity (P) for a specific condition, as shown by the following relationship between strength (K) and relative amplitude (β):

$$K = e^{5.2115 - 0.1444\beta}$$

The equation above is applicable to concrete with a moisture content of 3-4%, an age of ninety days, made from crushed granite aggregate with a maximum size of twenty mm, cured by immersing in water for twenty-eight days, and measured by the direct technique (receiving and transmitting transducers on opposing sides of the concrete sample) at 150 mm beam path distance without reinforcement bars. The relative amplitude decreases as the strength is increased. While the above equation is an example, such a relationship between strength and relative amplitude can be drawn from empirical testing.

When an impulse is transmitted through a material, the relative amplitude (β) is given by:

$$\beta = 20 \log \left( \frac{A_{ps}}{A_p} \right)$$

where $A_{ps}$ is the pressure wave amplitude after the arrival of the torsional wave, and $A_p$ is the pressure wave amplitude. Since the relative amplitude method sends an impulse through the concrete, it might also be used to correlate the size, type, and stiffness of any reinforcing fibers. This correlation is determined by sending impulses at various frequencies and analyzing the frequency response.

In some instances, only one side of the concrete sample may be accessible, such that thickness of a concrete sample is unknown. In such circumstances, or otherwise where it is desired to determine thickness of a concrete sample, the impact-echo method of determining concrete thickness may be used, as described in the ASTM C 1383 standard. The impact-echo test involves two modes of operation, both of which rely upon mechanical waves imparted to a concrete sample by an impact hammer. The impact hammer produces a mechanical impact on the concrete surface, generating multiple modes of vibration, including p-waves, s-waves and Rayleigh waves. The impact hammer includes a steel ball head in which is disposed a piezoelectric element that generates an electrical signal when the steel ball strikes the concrete sample. The impact hammer outputs this signal to a computer system, allowing the computer system to recognize that the test has begun and to therefore configure the system to receive the receiving transducer output.

The first part of the test determines p-wave speed, based on reception of the hammer-imparted p-wave detected by a pair of broadband transducers disposed on the same concrete surface at which the hammer imparts the mechanical wave. Both transducers may include piezoelectric elements that are coupled to the concrete surface. The receiving transducers are independently disposed on the concrete surface at a fixed distance, e.g. about 300 mm, apart. Although disposed on the concrete surface independently of each other, a spacer may be placed between them to fix the desired distance. The operator strikes a hammer on the concrete surface on the same line that includes the centers of the two receiving transducers, at a distance of 150+/−10 mm from the closest transducer, with an impact duration of 30+/−10 microseconds.

When the p-wave reaches the two piezoelectric receiver transducers, the transducers convert the mechanical energy to an electrical signal that is output to a computer. Upon reception of the signals from the receiving transducers, the computer determines the difference in time between the two signals, i.e. the p-wave's time of travel between the two receiving transducers, or ($\Delta t$). Since the distance (L) between the receiving transducers is known, the computer calculates p-wave speed ($C_p$) by dividing distance by travel time. P-wave speed in concrete is then converted to the apparent p-wave speed in a plate ($C_{p,\,plate}$=0.96 $C_p$).

The second part of the test determines the frequency of a standing wave generated by the hammer impact, i.e. the resonance frequency. A broadband transducer is manually disposed on the concrete surface, and the operator strikes the same concrete surface with the impact hammer near the transducer. The piezoelectric element at the impact hammer head outputs a signal from the hammer to the computer that triggers the computer to watch for a response from the broadband receiving transducer. The impact generates a p-wave that propagates into the concrete plate and reflects from the opposite surface. The return wave reflects, in turn, from the initial impact surface, and so on, giving rise to a transient thickness resonance. The broadband transducer converts the detected wave into an electrical signal that is output to the computer, which captures the output as a time domain waveform. The computer obtains a frequency domain signal through a windowing function and execution of a Fast Fourier transform. A Hamming window may be used to reduce ringing in the spectral values outside the windows. A sampling period may be two microseconds, using a 500 kHz clock and 1024 data points in the recorded waveform. The duration of the recorded waveform is 2048 microseconds, giving a spectral resolution of 488 Hz in the signal spectrum. There are 512 frequency channels, and the maximum sample frequency is 250 kHz. The computer displays 1024 samples in the time domain and 512 bins (250 kHz) in the frequency domain. The resonance frequency (f) appears as a peak in this waveform, which the software application identifies.

Thickness of the concrete plate is then given by the following equation:

$$T = \frac{C_{p,plate}}{2f}$$

The actual impact has a significant influence on the success of the impact-echo test. The estimate of the maximum frequency in the frequency domain excited is the inverse of the impact hammer's contact time at the concrete surface. Thus, a shorter contact time results in a higher range of frequencies contained in the pulse imparted into the concrete by the impact hammer, and the depth of the opposing surface (which may be the opposite surface of the concrete sample, or a defect or object located within the sample that creates an intermediate standing wave) which can be detected decreases according to the equation above. Short duration impacts are needed to detect opposing surfaces and defects that are near to the surface upon which the test is performed. Sansalone and Streett, "Impact-Echo: Nondestructive Evaluation of Concrete and Masonry," (1997), provide an estimate of the maximum frequency ($f_{max}$=291/D) for a steel ball bearing of diameter D, and it is known for an impact hammer to utilize interchangeable steel and stainless steel balls that vary in diameter. As steel ball diameter increases in the impact hammer, so does maximum detectable thickness.

Depending upon knowledge of the characteristics of the concrete sample, the concrete density may be known.

The ultrasonic pulse echo method may be used on one side of a concrete sample to determine both thickness and concrete characteristics in the sample when only one side of the sample is available. In particular, this method may be used to detect internal features, such as the location and density of rebar. The principle is based on the measurement of the time interval between transmitting an ultrasonic impulse into the sample and receiving an echo. The transit time (T) of the pulse to traverse twice the path length to (L) is measured, and the longitudinal pulse velocity ($C_p$) is given by:

$$C_p = \frac{2L}{T}$$

Ultrasound is highly attenuated in concrete, and for increasing thicknesses, it may therefore be difficult to effectively obtain an echo signal. Thus, to overcome the effects of wave scattering, and thus attenuation, caused by aggregates and air pores, the frequency of the ultrasound signal is typically low, and can be as low as 50 kHz.

To implement this method, two narrowband transducers are applied to the same side of the concrete sample, at a predetermined distance apart from each other. The computer system excites one of the two transducers, causing the transducer to impart a mechanical signal into the sample. The computer system is in communication with both the transmitting and receiving transducers, actuating the transmitting transducer and receiving the electrical signal from the receiving transducer. The signal received from the receiving transducer will include data describing both a surface wave and reflections. To remove the surface wave data, leaving the reflection data, the computer system applies a signal processing technique known as frequency-wave number filtering (FK filtering). FK filtering uses the slope of the data to selectively remove values that lie along a particular line (two dimensional filtering).

In essence, the pulse-echo method determines the time of flight of the mechanical pulse imparted into the concrete sample and reflected back from the opposing side of the sample or an intermediate object, such as rebar. By taking these measurements sequentially across a concrete sample, the most common detected distance is typically from the opposing sample side. Accordingly, anomalies of shorter distances that appear in the output data correspond to positions at which imbedded material may occur.

SUMMARY OF THE INVENTION

In a method of determining a characteristic of a concrete sample in an embodiment of the present invention, at least one broadband transducer is disposed in contact with a surface of a concrete sample. A first mechanical wave is imparted in the concrete sample at a position proximate to the broadband transducer so that a standing wave is established in the concrete sample and so that the standing wave is detectable by the at least one broadband transducer. The standing wave is detected at the at least one broadband transducer, and at least one corresponding output signal is generated. A resonant frequency of the standing wave is determined from the at least one broadband transducer output signal. A plurality of narrowband transducers are disposed in contact with the concrete surface at predetermined distances from each other. At least one of the narrowband transducers is actuated so that the at least one transducer imparts a second mechanical wave at the surface of the concrete sample. The second mechanical wave is received by at least one other narrowband transducer, and at least one respective output signal is responsively generated. Based on the at least one narrowband transducer output signal, a velocity of the second mechanical wave is determined. Based on the velocity of the second mechanical wave and the resonant frequency, a depth of a characteristic of the concrete sample is determined.

A device for determining characteristics of a concrete sample in another embodiment of the present invention includes an impact device for imparting a first mechanical wave to a concrete sample so that a standing wave is established in the concrete sample. The device includes at least one broadband transducer for detecting the standing wave and responsively generating an output signal, and a frame. A plurality of narrowband transducers is secured by the frame at predetermined distances with respect to each other and so that coupling surfaces of the narrowband transducers are generally coincident to a surface shape corresponding to a surface of the concrete sample. A control device is in communication with the broadband transducer and the narrowband transducers, and is configured to receive at least one output signal from the at least one broadband transducer, and actuate at least one of the narrowband transducers to impart a second mechanical wave at the surface of the concrete sample. The control device receives at least one output signal from and generated by respective at least one other of the narrowband transducers in response to reception of the second mechanical wave. The control device determines from the at least one broadband transducer output signal a resonant frequency of the standing wave. Based on the at least one narrowband transducer output signal, the control device determines a velocity of the second mechanical wave, and, based on the velocity of the second mechanical wave and the resonant frequency, determines a depth of a characteristic of the concrete sample.

In a further embodiment, a device for determining characteristics of a concrete sample includes a frame and a plurality of shear wave transducers secured by the frame at predetermined distances with respect to each other and so that coupling surfaces of the shear wave transducers are generally coincident to a surface shape corresponding to the surface of the concrete sample. A plurality of primary wave transducers is secured by the frame at predetermined distances with respect to each other and so that coupling surfaces of the primary wave transducers are generally coincident with the surface shape. A control device is in communication with the shear wave transducers and the primary wave transducers and is configured to actuate at least one of the shear wave transducers so that the at least one shear wave transducer imparts a shear wave in the concrete sample, and to actuate at least one of the primary wave transducers so that the at least one primary wave transducer imparts a primary wave in the concrete sample. The control device receives at least one output signal from respective at least one other of the shear wave transducers in response to reception of the shear wave by the at least one other shear wave transducer. The control device receives at least one output signal from respective at least one other of the primary wave transducers in response to reception of the primary wave by the at least one other primary wave transducer.

In an additional embodiment, a device for determining characteristics of a concrete sample includes a frame and a plurality of first transducers secured by the frame at predetermined positions with respect to each other and so that coupling surfaces of the first transducers are generally coplanar with each other, and a control device in communication with the first transducers and configured to actuate at least one of the first transducers so that the at least one first transducer imparts a mechanical wave in the concrete sample. The control device receives at least one output signal from respective at least one other of the first transducers in response to reception of the mechanical wave by the at least one other first transducer. Based on the received at least one output signal, the control device determines a depth of a characteristic of the concrete sample. The first transducers are arranged in the frame so that an area that is within a plane parallel to the coupling surfaces and in the concrete sample, and that is bounded within the plane by an extent of the mechanical waves that pass through the plane and that are receivable by the first transducers, has a dimension parallel to the coupling surfaces of at least about two feet.

In a still further embodiment, a device for determining characteristics of a concrete sample includes a frame and a plurality of first transducers secured by the frame at predetermined positions with respect to each other and so that coupling surfaces of the first transducers are generally coplanar with each other. A control device is in communication with the first transducers and is configured to actuate at least one of the first transducers so that the at least one first transducer imparts a mechanical wave in the concrete sample, and to receive at least one output signal from respective at least one other of the first transducers in response to reception of the mechanical wave by the at least one other first transducer. Based on the received at least one output signal, the control device determines a depth of a characteristic of the concrete sample. The first transducers are arranged in the frame so that an area that is within a plane parallel to the coupling surfaces and within the concrete sample, and that is bounded within the plane by an extent of the mechanical waves that pass through the plane and that are receivable by the first transducers, has a dimension parallel to the coupling surfaces at least as long as the distance between reinforcing bars in the concrete sample.

The accompanying drawings, which are incorporated in and constitute a part of this specification, illustrate one or more embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which:

FIG. 6 is a table illustrating operating characteristics of the device as shown in FIG. 1A;

Figure 1A:
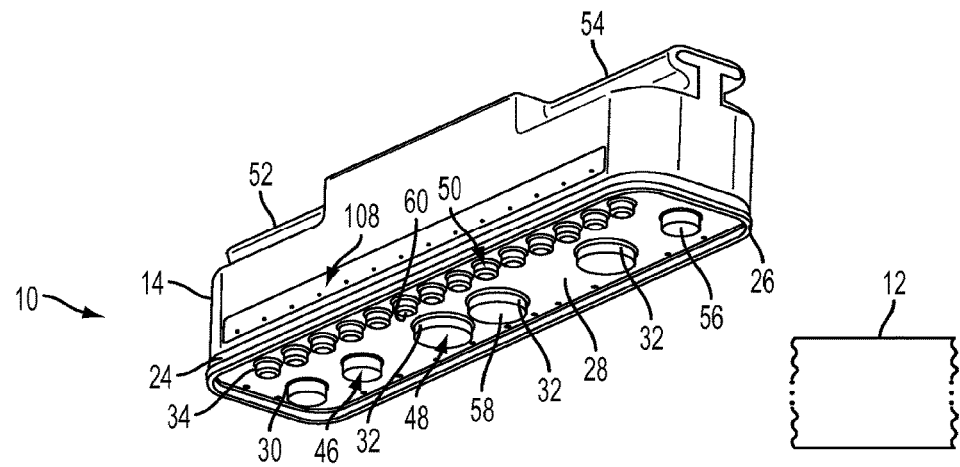
FIG. 1A is a perspective view of a device for determining characteristics of a concrete sample according to an embodiment of the present invention.
Figure 1B:
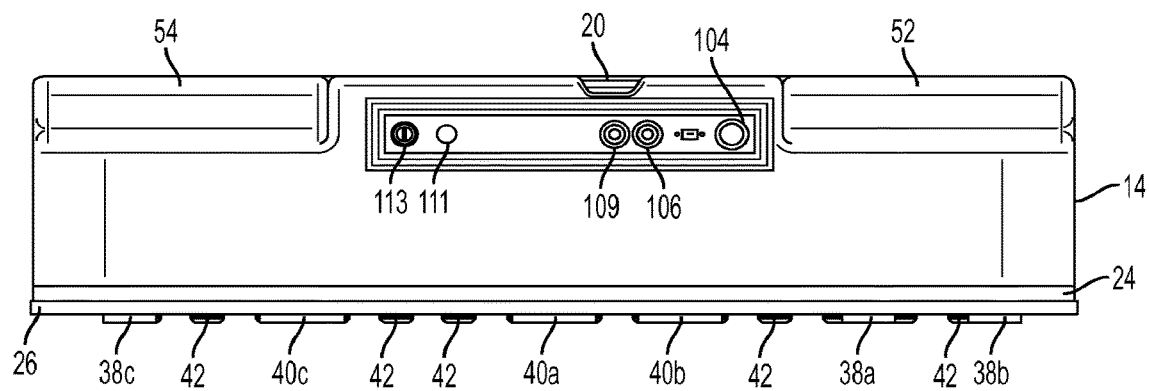
FIG. 1B is a side view of the device illustrated in FIG. 1A.
Figure 1C:
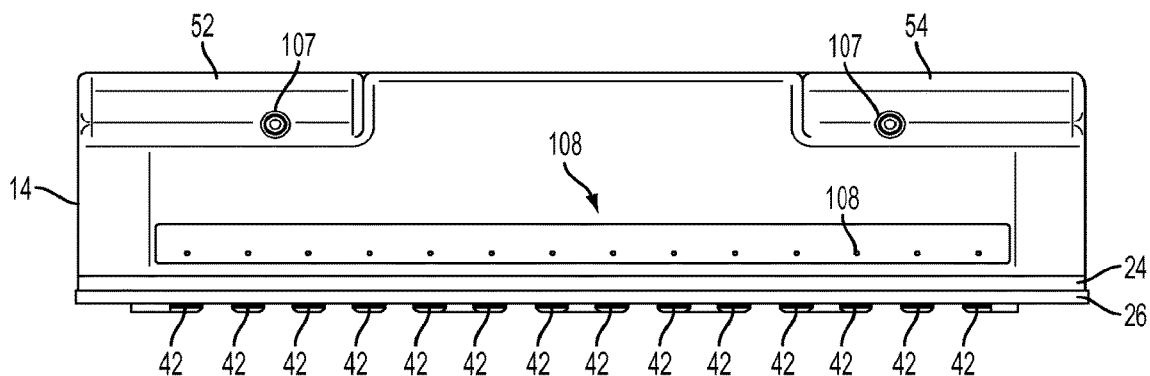
FIG. 1C is a side view of the device illustrated in FIG. 1A.

Repeat use of reference characters in the present specification and drawings is intended to represent same or analogous features or elements of embodiments of the present invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the present disclosure.

Referring to FIGS. 1A-1E and 2, a hand held device 10 for determining characteristics of a concrete sample 12, for example a wall, includes a housing 14 that encloses a transducer array unit assembly 16 and a control device comprised of a data acquisition unit assembly 18 and a controller unit 20. Housing 14 is made from a glass-filled NYLON 12, or other suitable thermoplastic or other material that, together with frame 22, forms a watertight device housing. Transducer array unit assembly 16 includes a frame 22 having a rim 24 that is generally rectangularly shaped and that is adhesively attached to a polymer trim 26 that receives rim 24 within a circumferential groove defined by trim 26. A gasket (not shown) is disposed between rim 24 and an open rim 27 of housing 14 to provide a watertight seal between the housing and the plate. The trim encloses the acoustic coupling surfaces of the transducers held by frame 22 when device 10 is pressed against a concrete surface, as discussed below, and serves as an electrical insulator between the electronics of device 10 and the concrete sample. Rim 24 of frame 22 attaches to rim 27 of housing 14 with a rubber gasket (not shown) between the rim and the housing to provide a water/dust seal.

Frame 22 includes a generally planar plate 28 that is bounded by rim 24 and that is continuous except for twenty circular holes at which corresponding transducer sleeves 30, 32, and 34 are attached or integrally formed. Each sleeve 30, 32, and 34 is cylindrical in shape and open at both ends. The openings in plate 28 correspond to the respective sleeve diameters. The metal at the sleeve base may be rounded at corners 36.

Each transducer sleeve 30, 32, and 34 has an inner diameter sized so that the sleeve receives a respectively sized transducer 38, 40, and 42. Each sleeve defines a pair of slots 44 that extend longitudinally (parallel to the sleeve axis) on opposite sides of sleeve's cylindrical body and that open to the open end of the sleeve opposite plate 28. Each transducer 38, 40, and 42 has a pair of pins or ridges 45 disposed on opposite sides of the transducer body and having a width corresponding to the width of the slot 44 in the sleeve in which the transducer is received. Sleeves 30 include one slot 44, for one corresponding rib 45 on transducers 38, and a larger slot to receive a BNC connector, but it should be understood that the sleeves can include two slots 44 to receive two transducer ribs 45. Each ridge extends sufficiently radially outward from the transducer's center axis so that the transducer's opposing pins or ridges 45 are slidingly received in the corresponding slots 44 as the transducer is received through the open sleeve top end and into the sleeve. The bottom edge of each pin or ridge 45 comes to rest at the closed bottom end of its corresponding slot 44, thereby defining the transducer's lower limit of travel toward and through the openings in plate 28.

Figure 2:
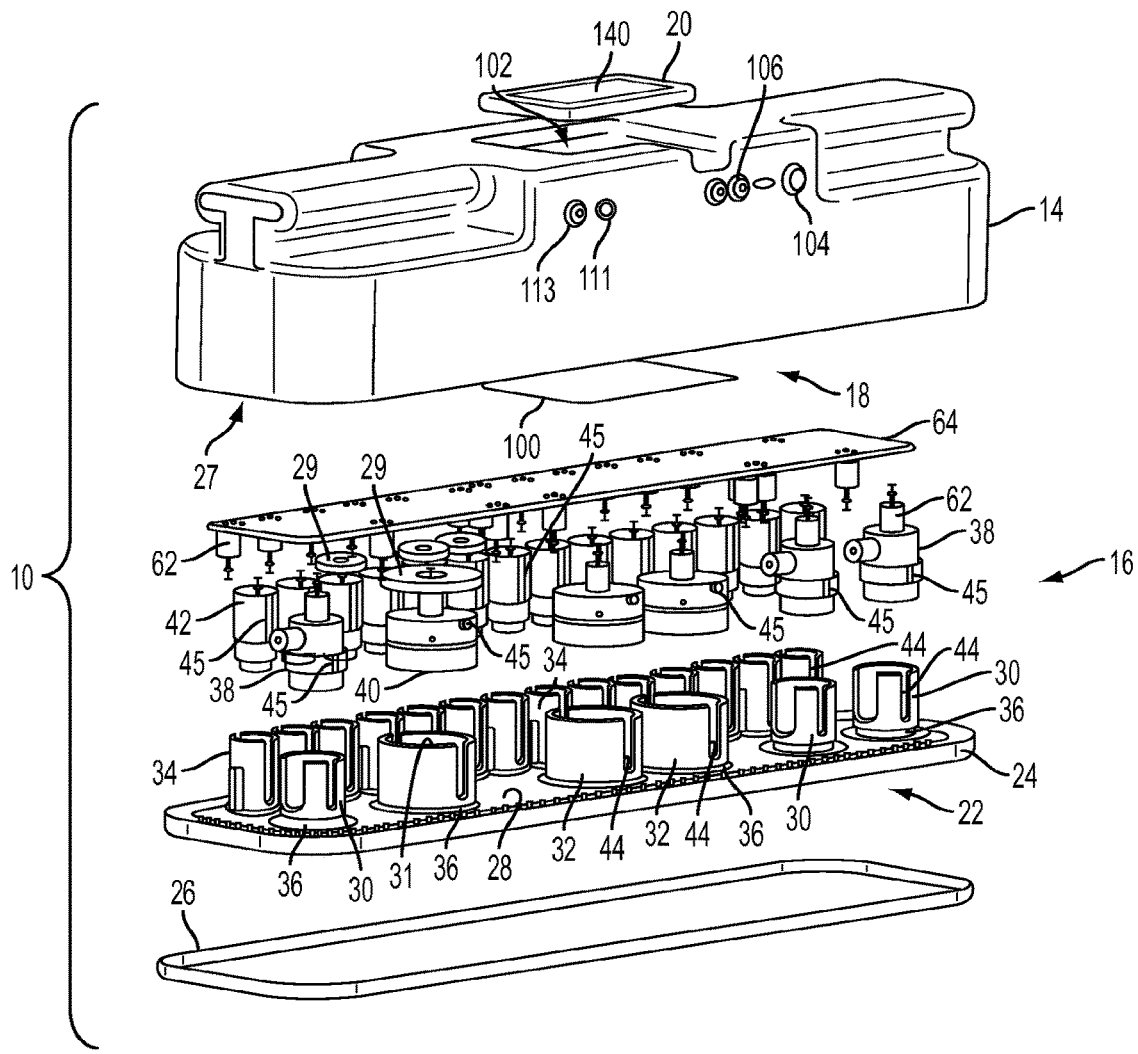
FIG. 2 is an exploded view of a device as in FIG. 1A.

Although sleeves 30, 32 and 34 are shown in FIG. 2 as open on their ends opposite plate 28, this is for purposes of clarity and explanation only, and in the assembly, each sleeve has a cap (see cap 29) that is secured to the open sleeve ends (see 31) to retain the transducers in the respective sleeves. As illustrated in FIG. 2, each transducer includes one or more BNC connectors 62 that deliver electrical signals to (in the case of transmitting) or deliver electrical signals from (in the case of receiving) the transducer. Each BNC connector is connected to a wired lead that extends (e.g. through the sleeve or cap) and connects to a corresponding BNC connector on board 64, thereby connecting the transducer to the board 64 circuitry. At each sleeve, a spring (not shown) is disposed between the cap and the transducer and biases the transducer away from the cap in the direction toward and through plate 28. When device 10 is not pressed to a concrete surface, the force of these springs pushes the transducers so that their ribs 45 engage the bottom of their respective sleeve slots 44. In this condition, the transducer coupling surfaces 46, 48 and 50 of respective transducers 38, 40 and 42 are coplanar, within a plane that is defined below (with respect to housing 14) the plane defined by the open end of trim 26. As the user presses device 10 to a concrete surface, therefore, the transducer coupling surfaces engage the concrete surface before trim 26, and as the user applies pressure to housing 14 until trim 26 engages the concrete surface, the concrete surface reaction force pushes the transducers back against their respective sleeve springs, causing the transducers to slide back into their sleeves in the slots 44, toward the sleeve caps. The resulting spring pressure facilitates the coupling of the transducer coupling surfaces to the concrete surface and causes a pliable, malleable solid coupling material (described below) between the coupling surfaces and the concrete surface to deform in a manner to fill air gaps between the transducer coupling surfaces and the concrete surface. It will be apparent, as well, that although the present discussion assumes a planar concrete surface, the individual transducer movement allowed by the sleeve/spring arrangement allows device 10 to be used as well on non-planar surfaces, as the transducers can accommodate some variation from a plane. The force applied by the individual springs may vary, but in the illustrated example each spring applies a force within a range of about one pound to about three pounds at the point at which the transducers have pushed back against the springs so that the transducer coupling surfaces are coplanar with the open end of trim 26. Because, as discussed below, the output signals from p-wave transducers 40 and s-wave transducers 38 are processed with automatic gain control, greater flexibility can be allowed in the force with which they contact the concrete surface, and in this example their springs apply a force near one pound. As also described below, however, the output signals from transducers 42 are not subject to automatic gain control, and in this example their springs apply a force of near three pounds.

When device 10 is placed on a generally planar concrete surface so that transducers 38, 40, and 42 operatively engage the concrete surface, all of coupling surfaces 46, 48, and 50 are disposed with respect to the concrete surface so that the given transducer can transmit or receive mechanical waves into or from the concrete sample at its operative frequency range, depending on its mode of operation in the system. Transducer coupling surfaces 46, 48, and 50 engage the concrete sample surface through solid coupling materials 56, 58, and 60, each sized correspondingly to the coupling surface of its transducer. Each coupling pad 56, 58, and 60 couples its corresponding transducer 38, 40, and 42 to the concrete by filling any spaces between the transducer coupling surfaces and the concrete surface, eliminating air gaps that could otherwise interfere with the transmission or reception of mechanical waves to or from the concrete. Such material should be pliable and malleable, so that it can conform into the air gaps, and may be made, for example, of suitable composites as should be understood. Preferably, the coupling material is thin relative to transducer wavelength to lessen an impedance effect. In alternative embodiments, the dry material may be replaced by gel or liquid coupling materials, as should be understood. The use of solid, gel, or liquid materials to couple transducers to materials such as concrete, should be understood and is therefore not discussed in further detail herein.

Transducers 38 are narrowband shear wave transducers, for example, as manufactured by CTS Valpey Corporation, of Elkhart, Ind., Model No. SS0.058. Transducers 40 are narrowband p-wave transducers, for example, such as manufactured by Proceq SA and Proceq USA, Inc., of Aliquippa, Pa., Model No. 32540130. The construction of narrowband transducers 42 is discussed in more detail below. Each of transducers 38, 40, and 42 has disposed about its outer circumference one or more elastic O-rings that engage the inner circumferential surfaces of their corresponding sleeves to assist in locating the position of the transducer and to provide a sealing engagement.

As should be understood, a piezoelectric transducer's bandwidth may be considered that part of the transducer's frequency response that is within 3 db (or half power) of the peak response. The transducer's Q, or quality, factor is the peak frequency in the response, divided by the transducer's bandwidth. A narrowband transducer is one that can be considered to operate at a single frequency, whereas a broadband transducer operates over a range of frequencies. The contrast between a single frequency and a range of frequencies depends on the context of the device, and thus the definition of what constitutes narrowband and broadband can vary as appropriate for the circumstances.

Transducer array unit assembly 16 also includes the printed circuit board 64 at which is disposed circuitry that controls voltage pulse amplifier, multiplexer, signal reception and processing, and LED functions, so that the transducers and control circuitry perform the functions described herein. Board 64 is received and secured in the interior of housing 14 so that when transducers 38, 40, and 42 are received in their respective sleeves 30, 32, and 34, and frame 22 is secured to housing 14, each of the transducers makes electrical contact with the circuitry of board 64 via BNC connectors and associated leads.

The transducer array includes three shear wave transducers 38 and three primary wave transducers 40. In each group of three transducers, the control device operates one transducer as a transmitter and the other two as receivers. The centers of the circular coupling surfaces of each p-wave and s-wave transducer can be considered the transducers' operative centers. Considering receiving shear wave transducers 38a and 38b, a line 66 passes through their centers, and transmitting shear wave transducer 38c is considered to be aligned linearly with its receiving transducers 38a and 38b in that its operative center also lies generally on line 66. Similarly, transducers 40 include a pair of receiving transducers 40a and 40b and a transmitting transducer 40c. The operative centers of transducers 40a and 40b also define a line that also generally passes through the operative center of transmitting transducer 40a. In this example, transducers 40 and transducers 38 are, additionally, collinear with each other so that all transducers 38 and 40 are generally aligned on line 66, although in other embodiments, the transducer groups are not collinear. Still further, the transducer groups 38 and 40 overlap in that transducers 40 are disposed between transmitting transducer 38c and the nearest receiving transducer 38b. Due to the collinear, spatially overlapped arrangement of the transducers, the mechanical waves transmitted and received by the two transducer groups at least partially share a common path through the concrete, thereby increasing the similarity of conditions experienced by the s-waves and the p-waves by reducing the impact of concrete's inherent non-homogeneity. This beneficially impacts the reliability of the resulting measurements.

The coupling surfaces of transducers 42 are also circular in circumference. In the illustrated embodiment, there are fourteen transducers 42 secured by plate 28, and the plate holds the transducers so that their operative centers are aligned collinearly generally along a line 68. Lines 68 and 66 are parallel to each other, although it should be understood that other arrangements are possible.

In the embodiment described herein, the diameters of the coupling surfaces of shear wave transducers 38, primary wave transducers 40, and primary transducers 42 are about 1.25, two, and one inch, respectively. Preferably, the transducers are acoustically isolated from the plate, e.g. by the elastic O-rings so that the transducers do not induce vibrations in the plate capable of actuating other transducers held by the plate. Considered along line 66, the operative centers of receiving p-wave transducers 40a and 40b are separated by a distance 70 of about three inches. The operative center of transmitting p-wave transducer 40c is separated from the center of its closest receiving transducer 40a by a distance 72 of about six inches. The centers of receiving shear wave transducers 38a and 38b are separated by a distance of 74 of about three inches, and the center of transmitting shear wave transducer 38c is separated from the center of its closest receiving transducer 38b by a distance 76 of about eighteen inches.

Considered along line 68, the centers of each pair of adjacent transducers 42 are separated by a distance 77 of about 1.5 inches, and the centers of the two furthest transducers 42 are separated by a distance 78 of about 19.5 inches. Generally, the separation between the two endmost transducers 42 is sufficient so that the measurements conducted by the linear array can be expected to detect the presence of rebar, even if the rebar is separated by its greatest expected separation, and regardless where the device is applied to the concrete sample. Considered from the viewpoint of a plane parallel to the coupling surfaces of transducers 42 within the concrete sample at a depth at which the rebar is expected, the linear dimension, parallel to line 68, of the intersection of the combined signal cones from and to the transducers 42 and this plane is at least as long as the longest expected separation of reinforcing bars.

Figure 1D:
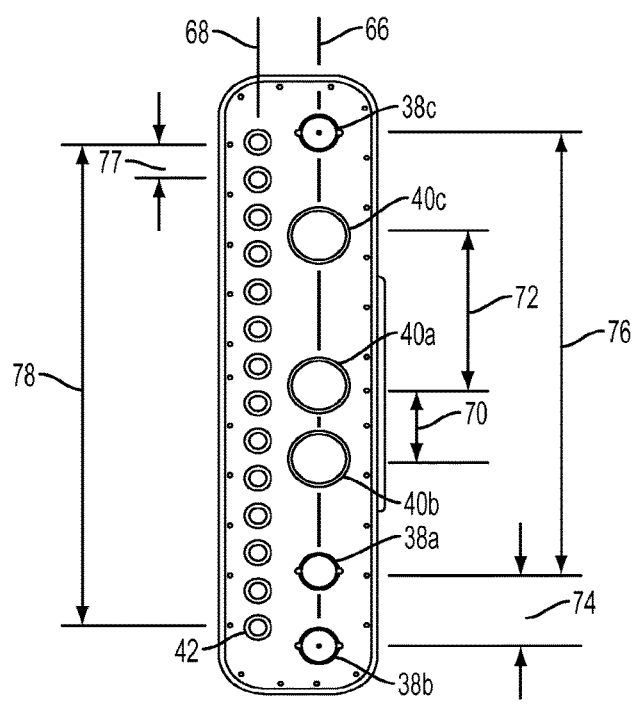
FIG. 1D is a bottom view of the device as in FIG. 1A.

As apparent from FIGS. 1A and 1D, the transmitting and receiving s-wave transducers 38 are separated by a longer distance than are the transmitting and receiving p-wave transducers. Because the p-wave component of the signal imparted by the transmitting s-wave transducer travels faster than the s-wave component, the longer separation between the shear wave transmitter and receivers allows greater separation between the wave components when they reach the receivers, decreasing the likelihood that the p-wave component contributes significantly to the detection of the s-wave component by the receiving s-wave transducers.

As described in more detail below, transducers 42 are actuated in sequential pairs, beginning at one end of the row along line 68. Consider, for example, the leftmost transducer 42 on line 68, in the perspective as in FIG. 1A (or, the bottommost transducer 42 in FIG. 1D). Upon actuation of a rebar location test described below, the control device excites this transducer to impart a mechanical pulse into the concrete surface and selects the transducer to its immediate right from which to receive an electrical signal corresponding to the resulting mechanical wave it detects. After a predetermined settling time, the control circuitry then actuates the second transducer 42 on line 68 (i.e., the immediately previously receiving transducer) to impart the next mechanical wave into the concrete sample, and selects the immediately adjacent transducer 42 to the right on line 68 from which to receive the next data signal. This cycle continues, with the operative pair of transducers 42 sequentially shifting one transducer to the right for each measurement, until the rightmost transducer 42 (or, topmost transducer, in FIG. 1D) functions as the receiving transducer. The control device then actuates the last (rightmost) transducer as the transmitting transducer, with the transducer immediately to the left as the receiving transducer. Accordingly, in one complete cycle of the fourteen transducers, all the transducers function as a transmitter, and all but the leftmost transducer function as a receiver (with the next to last right transducer operating as a receiver twice), and there are fourteen operative pairs of transducers within the group of fourteen transducers 42.

As noted, in the presently described example, the diameter of transducers 42 (including the transducer housing, although for purposes of explanation, this can also be considered the diameter of the transducer's coupling surface) is about one inch. This diameter is in turn related to the concrete characteristic that device 10 is configured to detect, in this instance steel reinforcing bars (rebar), and in particular to the resolution needed to detect the rebar. As should be understood, reinforcing bars in large, generally planar-type concrete elements, e.g. walls and slabs, are commonly spaced about six inches apart. Generally, however, rebar spacing can vary in typical concrete structures from about three inches to about eighteen inches. Because the minimum rebar spacing is expected to be about three inches, the array of transducers 42 should operate with a resolution of at least three inches if it is desired to maintain the capability to distinguish between adjacent bars. To accurately identify the rebar occurrences according to the Nyquist criterion without spatial aliasing, then, the maximum spacing between sampling points is half the desired resolution, or 1.5 inches. If it is assumed that each transmitting/receiving pair of transducers 42 detects the presence of rebar at points on a line bisecting the parallel axes of the two adjacent transducers, then these bisecting lines should be spaced apart by a maximum distance of 1.5 inches, and since each operative pair of transducers 42 is shifted one transducer spacing from the previous pair, this maximum distance is also the maximum distance between the centers of adjacent transducers 42. Because the distance between transducers corresponds to the distance between the transducers' centers, a maximum transducer spacing of 1.5 inches means that the transducers should be less than 1.5 inches in diameter, and to allow suitable isolation, preferably about one inch or less.

It should be understood, however, that larger-diameter transducers may be used within the scope of the present disclosure. In that event, unless the actual rebar spacing were known, and unless that spacing were within the device's resolution, the device would be able to identify the presence of rebar, but not confidently identify a given bar's position with respect to an adjacent bar. Accordingly, in such embodiments, the identifying array 108 of LEDs (described below) might be omitted in favor of a single LED or commonly activated LED array that is activated whenever the device identifies the presence of rebar.

Returning to the present example, because the maximum expected spacing of rebar is eighteen inches, and given the transducer spacing of about 1.5 inches, fourteen transducers are used in order to assure that when the device is pressed onto a concrete surface in two 90° offset positions, the linear array will detect rebar if it is present in the sample. This results in an array of transducers 42 of about 19.5 inches, with a resulting length of housing 14, in the dimension of lines 66 and 68, of about two feet. As should be appreciated by the present disclosure, however, the number, dimensions, and arrangement of transducers 42 may vary as desired, and in particular with respect to the concrete characteristic being measured. The device as presently described in these examples weighs about ten pounds, and in this example the about ten pound weight and about two feet maximum housing dimension allow the device to be used as a handheld device. It should be understood, however, that these dimensions and weight can vary, and for example the present invention contemplates the device 10 constructed at a weight less than about ten pounds and/or with a major dimension in a plane parallel to the plane of plate 28 shorter than about two feet.

Similarly, in other embodiments, parallel rows of transducers 42 may be utilized, i.e., a two-dimensional or other multi-dimensional array. Multi-dimensional arrays may be desirable, depending on the measured-for characteristic. In this presently-described example of an array utilized for detecting rebar, however, a linear array is effective and also beneficially reduces the size of device 10. Because rebar is typically disposed in concrete as parallel bars, an operator may make two measurements at a 90 degree offset with respect to each other, but otherwise at the same or similar location on the concrete surface, and have confidence that if the rebar is uniformly distributed within the concrete sample, one or both of these two measurements should detect its presence.

Figure 3:
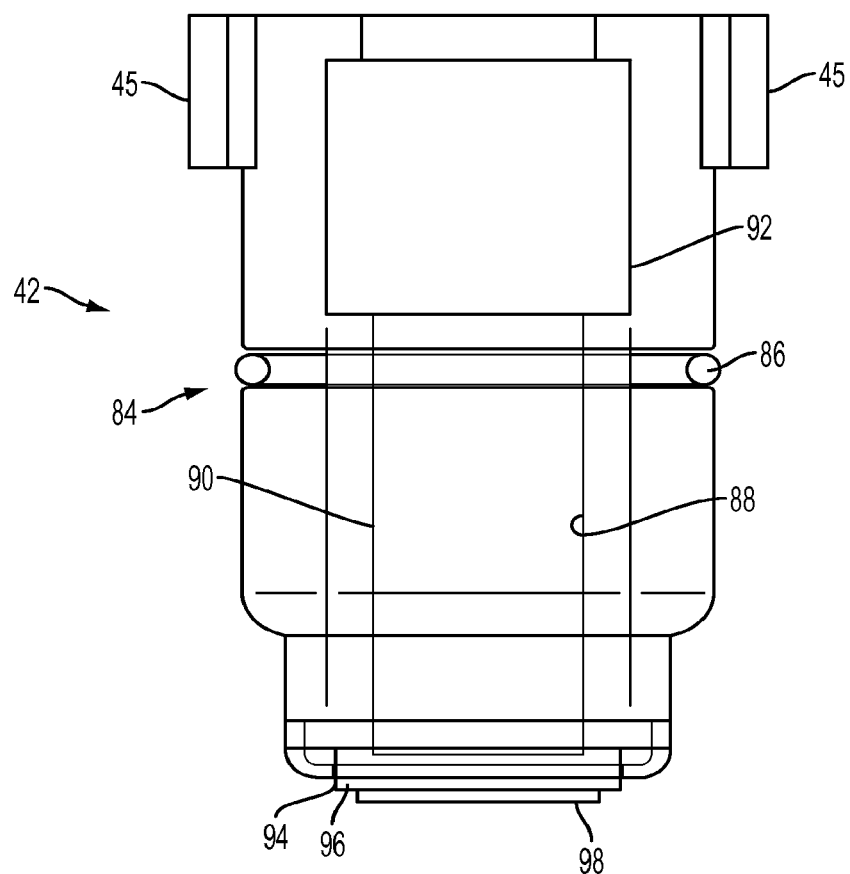
FIG. 3 is a schematic illustration of a narrowband transducer used in the device as shown in FIG. 1A.

Referring to FIG. 3, each transducer 42 has a generally cylindrical housing 82 made of polyether ether ketone, or PEEK, that defines a generally central groove 84 in which is disposed an elastic O-ring 86 that engages the inner circumference of the transducer sleeve 34 (FIG. 2) in which the transducer is received. Housing 82 defines a generally cylindrical inner bore 88 in which is disposed a piezoelectric element 90 formed of a piezoelectric epoxy composite material, for example a piezoelectric ceramic known as PZT-5H2, that has a thickness of approximately one inch, an acoustic impedance of 12.1 MRayls, and a resonance frequency of 56 kHz. A backing material 92 fills a chamber immediately behind piezoelectric element 90. Backing 92 is a dielectric material that holds the piezoelectric element 90 in place and dampens ringing in the piezoelectric element after the initial pulse. In one embodiment, backing 92 is comprised of particles of various sizes of tungsten mixed with an epoxy resin in a ratio such that the composite has a resultant acoustic impedance of 12 MRayls. A front face 94 is disposed at the forward end of piezoelectric element 90 and defines the coupling surface 96. Front face 94, in this example, is made of a glass ceramic, for example sold under the name MACOR available from Corning, Inc., of Corning, N.Y., that has an acoustic impedance of 11.7 MRayls. Front face 94 acts as a buffer plate that protects piezoelectric element 90 from the rough concrete surface and that is stable at high temperatures without significant thermal expansion. The front face reduces the impedance mismatch between the piezoelectric element and the concrete surface. A thin dry solid couplant layer 98 (identified as 60 in FIG. 1A) couples the transducer to the concrete by filling any gaps between front face 94 and the concrete surface, eliminating air gaps that could otherwise interfere with the transmission of mechanical waves to the concrete from the transducer.

As should be apparent from the present disclosure, the transducers described herein may operate in the acoustic or ultrasonic frequency ranges, but for purposes of explanation may be referred to generally as acoustic transducers having acoustic coupling surfaces.

Data Acquisition Unit 18 includes a printed circuit board 100 that houses a main microprocessor that controls the operation of device 10, as well as a dedicated microprocessor for automatic gain control. The organization and operation of the circuitry of board 100 is discussed in more detail below. Batteries and a sealed battery compartment (not shown) may be provided in housing 14 as a power source, and/or DC power may be supplied by an external power source via a power input port in housing 14.

The control device also includes a controller unit 20, in this example a mobile computing device that comprises one or more microprocessors that execute an operating system that supports programmable computing features and the installation of application programs. Mobile device 20 includes input/output capability that allows operative connection to the control circuitry at board 100. Device 20 also includes a display driven through the operating system by a graphical user interface, as described below. In one embodiment, controller unit 20 is a commercially-available "smart phone" that is received in a correspondingly shaped cavity 102 in housing 14. A cover plate (not shown) may be provided at housing 14 to hold controller unit 20 in place. It should be understood that controller unit 20 can comprise another type of computing or mobile device, such as a tablet, or may comprise a dedicated processor and related circuitry disposed on a circuit board secured within a corresponding cavity 102.

A LEMO connector 104 allows communication between the microprocessor at board 100 and an impact hammer/broadband transducer assembly 176 (FIG. 7), as described below. A pair of test initiation buttons 107 (FIG. 1C) are also mounted in housing 14 near handles 52 and 54 (for ease of access by the user holding the device) and are connected to the microprocessor at board 100 through a general purpose input/output to establish an actuation signal, as described below. A master switch 109 selectively switches a USB connector (located between an on/off switch 106 and LEMO connector 104) between operation as a power jack and as a means for connecting an alternate computer device. On/off switch 106 activates and deactivates device 10 and its power source. A fuse is provided in a holder 113, and a DC power input jack is provided at 111. Fourteen LEDs of linear array 108 are mounted in housing 14 and are driven by an LED driver board portion of board 64 and controlled by the microprocessor at board 100. As described below, those LEDs correspond to transducers 42, and in the illustrated example, the LED array is aligned proximate the bottom edge of housing 14, and the LEDs approximately spaced, so that the LEDs are spatially aligned with respective transducers 42.

Figure 7:
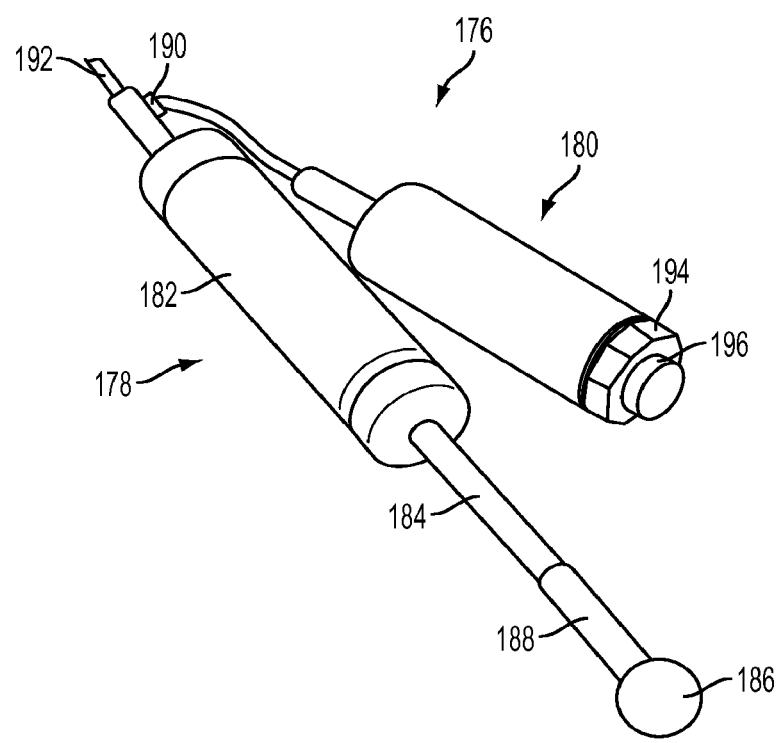
FIG. 7 is a schematic illustration of an impact hammer and broadband transducer for use with the device as in FIG. 1A.

Referring to FIG. 7, a transducer/impact hammer assembly 176 includes an impact hammer 178 and a broadband transducer 180. Impact hammer 178 includes a hand grippable handle 182 from which extends a semi-rigid hollow polymer tubing 184, at the end of which is interchangeably disposed a one-and-three-eighths inch (or other size, as selected by the user) steel ball 186. A piezoelectric element is disposed within steel ball 186 and is connected to an output wire (not shown) at a sheathing 188. The output wire extends through handle 182 to a harness 190 at which the wire is insulated from, but mechanically joined to, an input/output wire to broadband transducer 180, in an overall device communication wire 192. Wire 192 has a communication jack (not shown) disposed on its opposing end, for insertion in LEMO connector 104 (FIG. 2).

As discussed herein, the actual impact applied by hammer ball 186 has a significant influence on a success of the test, and impact hammer 178 utilizes interchangeable steel balls that vary in diameter accordingly. As steel ball diameter increases, the detectable resonant frequency of a signal imparted by the hammer decreases, and the maximum detectable sample thickness thereby increases. The one-and-three-eighths inch ball is effective at least for concrete walls of about two, three and six feet in thickness, although it should be understood this may vary. Because the direction of the mechanical wave imparted to the concrete varies directly with the size of the steel ball, and because the impact's duration should be shorter than the time needed for the resulting wave to traverse the sample's thickness, a smaller steel ball may be used where concrete thickness is expected to be low.

Transducer 180 includes a steel housing 194 that encloses an internal transducer assembly constructed generally similarly to the transducer described with respect to FIG. 3, with a spring biasing the internal transducer assembly so that the internal transducer assembly's front face 196 extends forward at the distal portion of transducer 180. The broadband transducer comprises a piezoelectric crystal mounted on a tungsten epoxy backing containing tungsten particles of 250, 25, and less than 1 micron in diameter. Electrical connections pass through the backing to the crystal. A MACOR facer is disposed in front of the crystal and defines the transducer's coupling surface. The piezoelectric crystal is preferably composed of an epoxy/PZT composite having an acoustic impedance of 12 MRayls with an operation between zero Hz and 50 KHz, but the ratio of PZT to epoxy can be adjusted to match the workpiece material. As described above, a solid, dry coupling material is secured to the acoustic coupling surface of the piezoelectric transducer element in order to couple the transducer element to the concrete surface. The dry contact pad has a similar response curve to the ultrasonic gel that is commonly used in acoustic testing.

Figure 4:
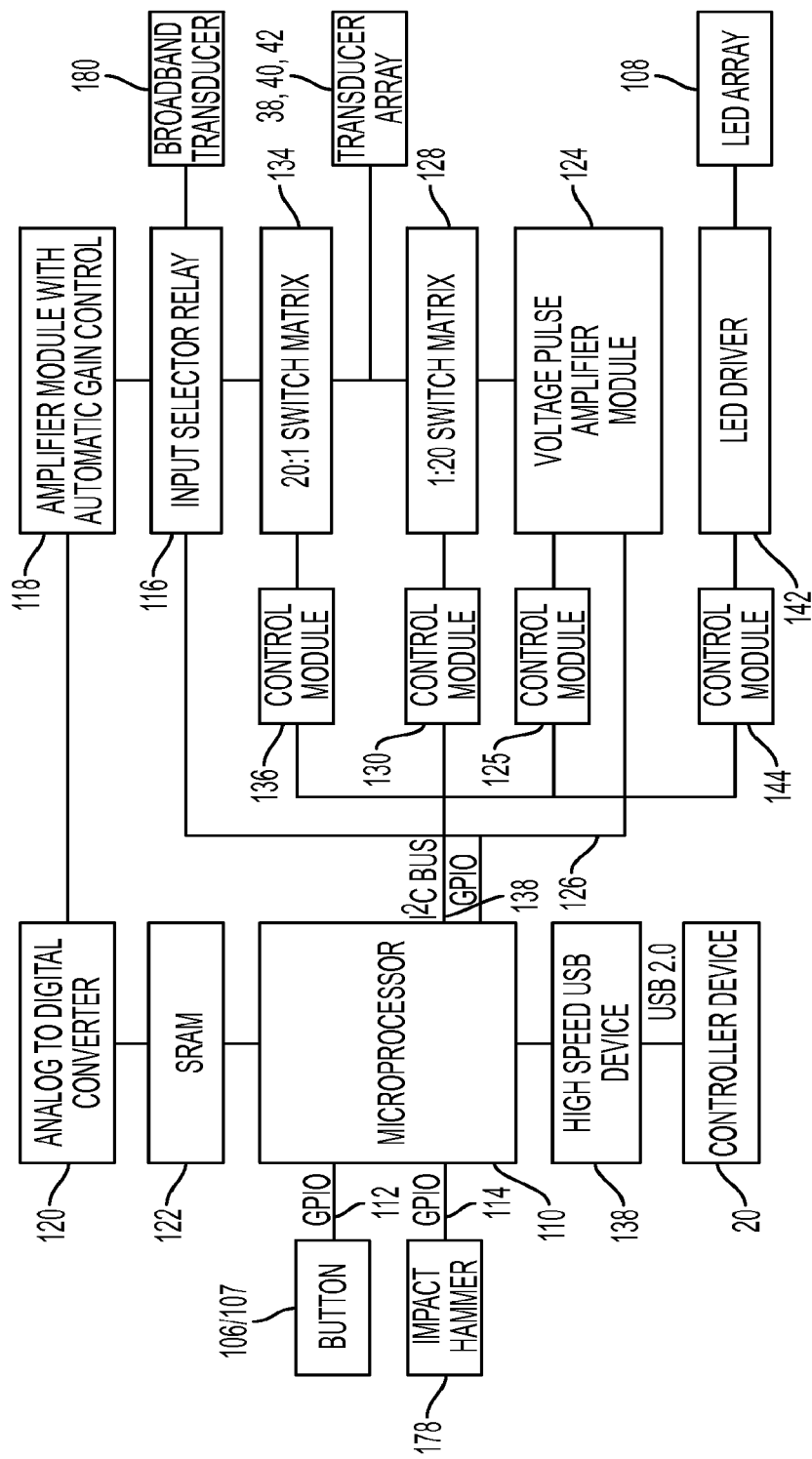
FIG. 4 is a schematic block diagram of control circuitry utilized in the device as in FIG. 1A.
Figure 5:
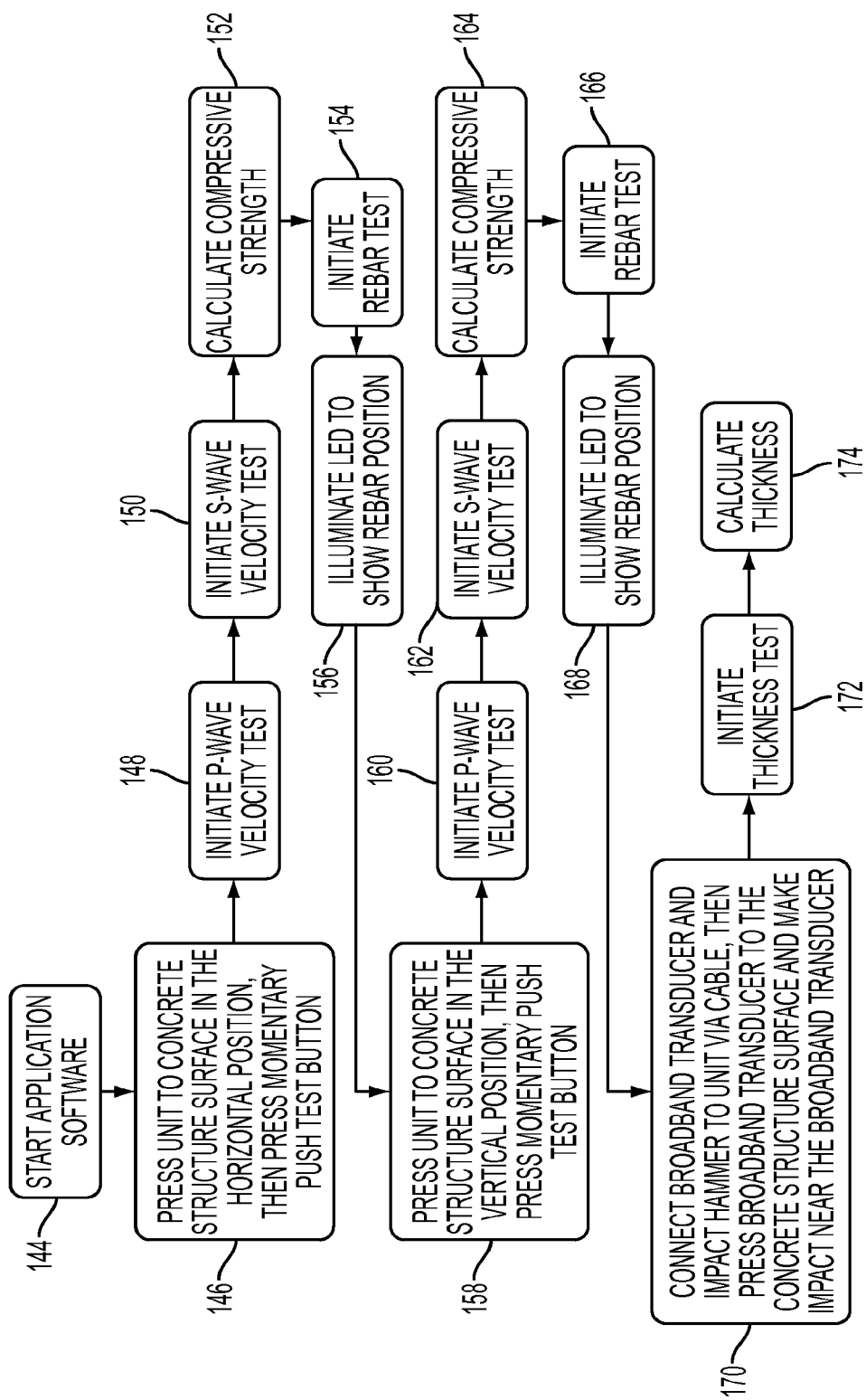
FIG. 5 is a flow chart illustrating steps performed by application software located at the control system of the device illustrated in FIG. 1A.
Figure 10A:
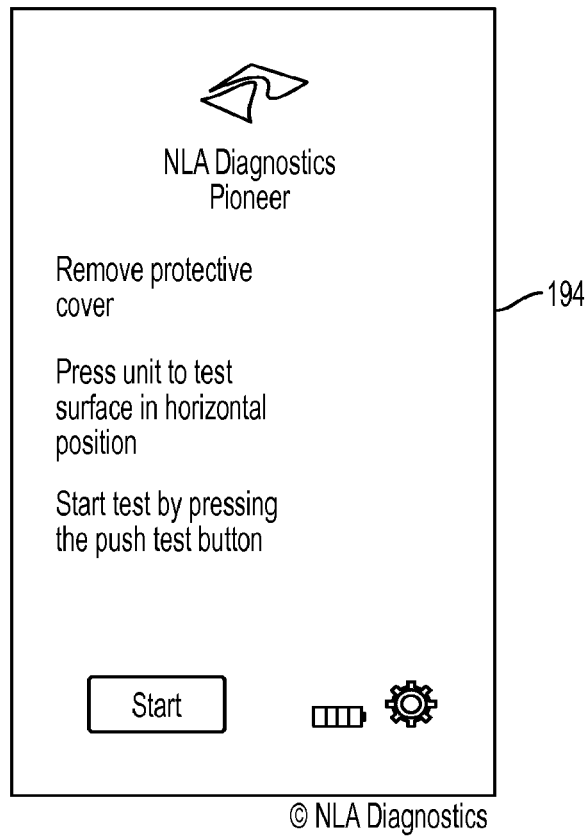
FIGS. 10A-10E are screen displays of a graphical user interface operated by the device illustrated in FIG. 1A.

FIG. 4 provides a schematic functional diagram of the control device and certain devices with which it interacts, and FIG. 5 illustrates the operation of device 10 from the perspective of application software operating on controller unit 20. A microprocessor 110 generally controls the operation of the concrete characteristic tests described herein (as controlled in turn by the application software), the provision of data to controller unit 20, and the operation of LED array 108. When the user actuates a start button (not shown) provided by a graphical user interface drive by application software that operates on controller unit 20 and that provides a screen display through which the user responds via a touch screen, the application begins operation, at 144. At 146, the application software may, in one embodiment, query the user (via a display 140 (FIG. 2) and graphical user interface at controller unit 20) to enter an expected rebar depth. Upon receiving a response, or in another embodiment, without a rebar query, directly upon receiving the user start button instruction, the application software causes the graphical user interface to display (at 194, FIG. 10A) instructions to the user to press device 10 (FIG. 1A) to the desired surface of the concrete sample 12, so that the coupling surfaces of transducers 38, 40, and 42 (FIGS. 1A-1E) engage the concrete surface, and to press one of the two test initiation buttons 107 proximate handles 52 and 54. The application program then enters a waiting mode, waiting for receipt of a signal from microprocessor 110 that a button 107 has been actuated and detected by the microprocessor over a general purpose I/O 112. When controller unit 20 receives this signal, the application software causes the controller unit to send a signal back to microprocessor 110, instructing the microprocessor to initiate a p-wave velocity test. In response, at 148, microprocessor 110 adjusts the output voltage level of a voltage pulse amplifier module 124 via general purpose I/O 126 and a control module 125. In the presently described example, the pulse amplifier module is variable, so that microprocessor 110 controls the amplifier module to produce an actuating pulse over a range of amplitudes up to about 1000V and at a desired pulse width. The length of the pulse is programmable via the application software between 2 and 20 microseconds. Thus, the signal from microprocessor 110 includes parameters sufficient to establish the amplitude, frequency, and time duration of a pulse initiated by the amplifier module. Control module 125 comprises circuitry that translates the microprocessor instructions into suitable signals to drive the amplifier module. The configuration and function of circuitry such as control module 125, as well as control modules 130, 136, and 144, discussed below, should be well understood and are therefore not discussed in further detail.

In the presently described example, the resonant frequency of p-wave transducers 40 is about 54 kHz. As should be understood, mechanical waves attenuate in concrete, and a relatively low frequency is therefore preferred in this example for the p-wave and s-wave transducers, although it should be understood that the frequency can vary as desired, provided the response signal can be acquired. Accordingly, the instruction from microprocessor 110 is to generate a pulse at 54 KHz, although the pulse frequency is selectable between about 50 kHz and about 120 kHz. Further, as discussed below, the presently illustrated p-wave velocity test is based on a p-wave time-of-flight from transmitting transducer 40c to each of the receiving transducers 40a and 40b. Provided the receiving transducers' output signals are sufficiently strong that the received p-wave can be detected over noise, then, the velocity test is based on identification of time differential rather than the ability to distinguish a particular amplitude level. That is, information is carried by a signal's time component rather than its amplitude component. This introduces the possibility of error arising from rise times. Because amplitude is not an information carrier, however, and because rise times can be improved by increasing signal amplitude, microprocessor 110 in the present example instructs the amplifier module to generate a pulse of about 592V (although amplitude can be varied as desired up to about 1000 v, which at the spacing of about six inches between transmitting transducer 40c and first receiving transducer 40a and of about nine inches between transducer 40c and second receiving transducer 40b, drives the receiving transducers into saturation upon receipt of the resulting p-wave.

Simultaneously, microprocessor 110 actuates a 1:20 switch matrix 128 (via a control module 130) to direct the output of amplifier module 124 to p-wave transducer 40c. Switch matrix 128 is a switching module comprised of discrete electronic components that can selectively direct the output of amplifier module 124 to any of transducers 38c, 40c and the fourteen transducers 42, as discussed above.

When voltage pulse amplifier module 124 is ready to transmit, it sends a pulse to microprocessor 110 that, in turn, notes the time and sends an instruction signal back to module 124, causing module 124 to drive transducer 40c that, in turn, imparts a mechanical wave into the concrete sample, resulting in a dominant p-wave that travels to transducer 40a.

Also via bus 132, microprocessor 110 actuates a 20:1 switch matrix 134 via a control module 136 to direct the output from receiving transducer 40a to an input selector relay 116. Relay 116 is a small solenoid relay that acts as a two-way switch, though as should be understood, an electrical switch could be used. Microprocessor 110 controls relay 116 to move to one of its two states, at which the relay directs the output of switch matrix 134 to an amplifier module 118. Amplifier module 118 outputs the transducer output to an analog-to-digital converter 120 for storage at a static random access memory 122 and retrieval by microprocessor 110. Thus, the receiving transducer 40*a* detects the resulting wave and outputs a corresponding analog signal to amplifier module 118 via switch 134 and relay 116. Amplifier module 118 applies an automatic gain control function to bring the signal strength to a desired level for acquisition by the system components. The amplified analog signal is converted from analog to digital by converter 120 and saved in SRAM 122. Microprocessor 110 controls the sampling load and the number of samples taken by converter 120.

Microprocessor 110 acquires the data from SRAM 122 in real time, and thus can analyze the retrieved data relative to the time the microprocessor received the pulse from amplifier module 124 at actuation of the p-wave. In one embodiment, the microprocessor directs the retrieved data, and the time at which the transmitting transducer was actuated, up to controller unit 20, where the application software analyzes the retrieved data and determines the point at which the represented signal (FIG. 8A) exceeds a predetermined threshold indicating reception of the p-wave at the receiving transducer 40*a*. The threshold can be determined through testing and calibration. Upon locating the p-wave reception, the controller unit determines the time difference (i.e. the time of flight) between the actuation of the transmitter transducer to impart the p-wave into the concrete and the reception of the wave by the receiving transducer. In another embodiment, the microprocessor conducts the analysis and provides results to the controller unit.

After a sufficient time for settlement, the microprocessor again instructs voltage pulse amplifier 124 to ready a p-wave pulse for transducer 40*c* but now instructs 20:1 switch matrix 134 to direct the output of second receiving transducer 40*b* to relay 116 and, therefore, to amplifier 118. Through an otherwise identical process, microprocessor 110 or the controller unit determines the time period between initiation and reception of the resulting p-wave between transducers 40*c* and 40*b* (see FIG. 8B).

Figure 8A:
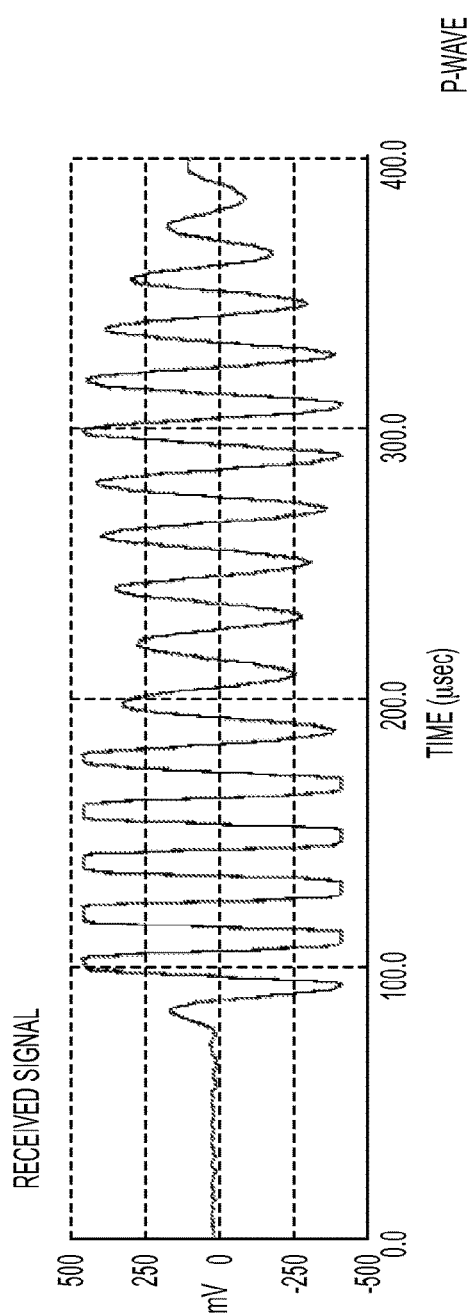
FIGS. 8A and 8B are graphical illustrations of signals generated by transducer of the device illustrated in FIG. 1A.
Figure 8B:
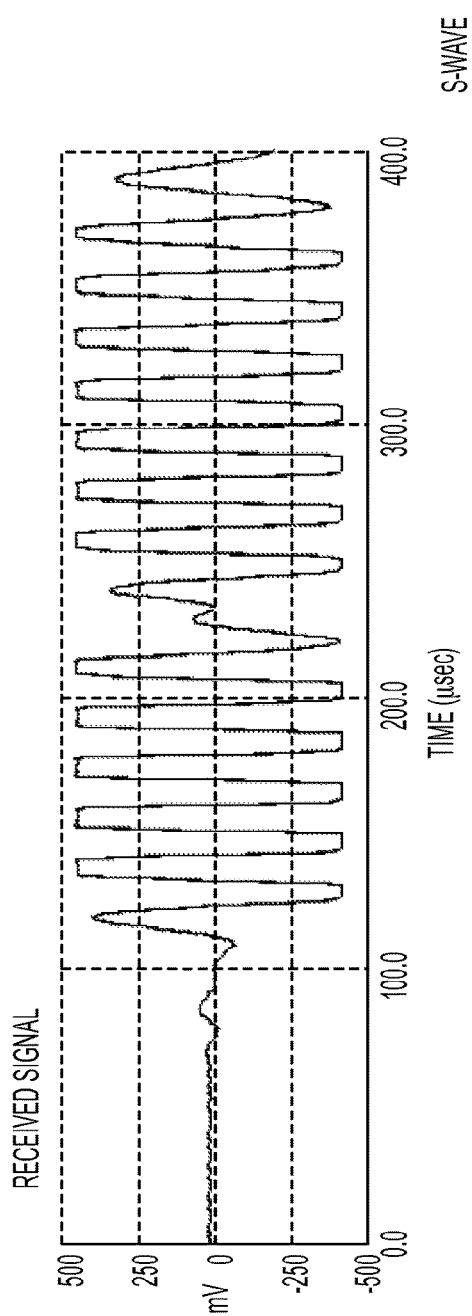

The application software (either directly from its analysis or upon receiving time of flight results from microprocessor 110) determines a difference between the two times of flight, which is in turn due to the difference in propagation time of the p-waves between the two transducers 40*a* and 40*b*, as illustrated by comparison of the signal representations provided by FIGS. 8A and 8B. Because the application software also knows the distance between transducers 40*a* and 40*b*, the application software determines the p-wave velocity by dividing the known distance by the differential time period.

At 150, the application software causes controller unit 20 to send a signal to microprocessor 110, causing the microprocessor to initiate the s-wave velocity test. Microprocessor 110 adjusts the output voltage level of voltage pulse amplifier module 124 via control module 125 and selects s-wave transducer 38*c* to connect to the output of amplifier module 124 via control of switch matrix 128 by control module 130. Microprocessor 110 also selects, through switch matrix 134 and control module 136, the output of transducer 38*a* to output to amplifier module 118 via actuation of input selector relay 116. When voltage pulse amplifier module 124 is ready to transmit, it sends a pulse to microprocessor 110 that, in turn, sends an instruction signal back to module 124, causing module 124 to drive transducer 38*c* that, in turn, imparts a mechanical wave into the concrete sample, resulting in an s-wave that travels to transducer 38*a*. The receiving transducer detects the resulting wave and outputs a corresponding analog signal to amplifier module 118 via switch 134 and relay 116. Amplifier module 118 applies an automatic gain control function to bring the signal strength to a desired level for acquisition by the system components. The amplified analog signal is converted from analog to digital by converter 120 and saved in SRAM 122. Microprocessor 110 controls the sampling load and the number of samples taken by converter 120.

As should be understood, the transducers described herein impart both p-waves and s-waves into the concrete. Although transducer 38*c* is an s-wave transducer, and although the resulting s-wave imparted to the concrete by transducer 38*c* is the dominant wave, i.e. is much larger in amplitude than the imparted p-wave, the p-wave travels faster through the concrete than does the s-wave, with the result that the leading edge of the p-wave will reach the receiving s-wave transducer before the leading edge of the s-wave. Thus, although the s-wave amplitude is much higher than the p-wave amplitude, to the extent the p-wave amplitude is higher than the threshold amplitude, controller unit 20 (or microprocessor 110) could interpret the first-received p-wave to be the arrival of the s-wave without programming to discriminate between the two (such programming being employed in another embodiment). Accordingly, in the present example, microprocessor 110 instructs voltage pulse amplifier 124 to prepare a pulse of an amplitude sufficiently low that the resulting s-wave reaching the receiving transducer will cause the receiving transducer to output a signal that will exceed the threshold applied by the microprocessor for recognizing receipt of an s-wave but so that the signal from the receiving transducer corresponding to the first-received p-wave will not. Accordingly, in this example, the microprocessor instructs the voltage pulse amplifier module to prepare a 42 v (peak to peak) at 50 KHz (the s-wave transducers' resonant frequency) at a width of about 8.4 microseconds.

Microprocessor 110, having acquired the sample data, directs the data to the controller unit, at which the application software (or the microprocessor) determines the s-wave time of flight in the same manner as it determined the p-wave time of flight. The application software knows the time at which the microprocessor instructed actuation of the transmitting transducer and the time at which the microprocessor acquired the output signal from the respective receiving transducer. The difference between these times is the time of flight.

At completion of this data acquisition, and after a settling period, microprocessor 110 repeats the sequence with the same transmitting transducer 40*c*, but now utilizing transducer 40*b* as the receiving transducer. The microprocessor instructs the amplifier module to prepare a second s-wave pulse, instructs switch matrix 134 to direct the output of second receiving s-wave transducer 138*b* to relay 116 and amplifier 118, triggers application of the input pulse to the transmitting transducer, and directs the resulting data to controller unit 20 so that the application software determines a time of flight of the resulting s-wave between transmitting transducer 38*c* and second receiving s-wave transducer 38*b*.

The application determines a difference between the two times of flight, which is in turn due to the difference in propagation time of the s-waves between the two transducers 38*a* and 38*b*. Because the application software also knows the distance between transducers 38*a* and 38*b*, the application software determines the s-wave velocity by dividing the known distance by the differential time period.

Given the now-determined p-wave velocity (CP) and s-wave velocity (CS), and assuming a concrete density of 2.38 g/m3, at 152 the application software relates these three variables to concrete compressive strength, based on the following model provided by the Architectural Institute of Japan (AIJ):

$$E = k1486\sigma^{1/3}\rho^2$$

The p-wave velocity ($C_p$) and shear wave velocity ($C_s$) are correlated to the Young's modulus (E), Poisson's ratio (v), and density ($\rho$) of the material as determined by the following equations:

$$C_p = \sqrt{\frac{E(1-v)}{\rho(1-2v)(1+v)}}$$

$$C_s = \sqrt{\frac{E}{2\rho(1+v)}}$$

The p-wave modulus (M) is correlated to p-wave velocity ($C_p$) and density ($\rho$) of the material as determined by the following equation:

$$M = \rho C_p^2$$

The shear modulus (G) can be correlated to shear velocity ($C_s$) and density ($\rho$) of the material as determined by the following equation:

$$G = \rho C_s^2$$

The Poisson's ratio (v) is correlated to the p-wave modulus (M) and shear modulus (G) as determined by the following equation:

$$v = \frac{M-2G}{2M-2G} = \frac{C_p^2 - 2C_s^2}{2(C_p^2 - C_s^2)}$$

The Young's modulus (E), also identified as the modulus of elasticity, is correlated to shear modulus (G) or p-wave modulus (M) and Poisson's ratio (v) as determined by the following equation:

$$E = 2G(1+v) = \frac{M(1+v)(1-2v)}{(1-v)}$$

As noted above, modulus of elasticity of concrete is frequently expressed in terms of compressive strength, but actual correlation between the two involves a model that can account for variations in concrete properties and binder/aggregate proportions. These models, in turn, tend to be applicable to ranges of concrete strengths. The American Concrete Institute (ACI) Committee 318 recommends, for example, a model to predict the modulus of elasticity for a wide range of concrete compressive strengths, from 200 psi to 3,000 psi, but that overestimates the modulus of elasticity for compressive strength over 6000 psi. The ACI Committee 363 recommends a model for higher strength concretes ranging from 3000 psi to 12,000 psi. The Architectural Institute of Japan (AIJ) recommends the equation above to predict modulus of elasticity for high-strength concretes ranging from 2,900 psi to 23,200 psi, and it is believed that the AIJ test successfully predicts the modulus of elasticity up to about 28,000 psi. Although it should be understood that various models may be employed within the scope of the present disclosure, in the present example the application software utilizes the AIJ model, for prediction of modulus of elasticity for compressive strength up to about 28,000 psi. That is, upon determining the p-wave velocity ($C_p$) and s-wave velocity ($C_s$) for a given test, and assuming a density for concrete, the application software correlates those determined and assumed values to Poisson's ratio (v) and Young's modulus (E). Then, and again assuming a concrete density, the AIJ model above relates the determined Young's modulus (E) to compressive strength ($\sigma$), where $k=k_1*k_2$, $k_1$ is a correction factor corresponding to coarse aggregates, and $k_2$ is a correction factor corresponding to mineral admixtures. In the presently described embodiment, concrete density is assumed to be 2.38 g/m³, and k is assumed to be one. In another embodiment, however, the application software queries the user to enter an actual density prior to the test's beginning, and if the user enters a value (through the graphical user interface and screen 140), the application software determines compressive strength based on the entered density value. Otherwise, the application uses the 2.38 g/m³ by default. Further, it should also be understood that the default values for density and k may change as desired, for example as determined through destructive compressive strength testing of concrete samples of known density and aggregate/admixture characteristics.

Upon determination of the compressive strength at 152, the application software stores the result and causes controller unit 20 to send a signal to microprocessor 110 to initiate the rebar test, at 154. In response, microprocessor 110 sends a command to control module 130 to set up the first (leftmost in FIG. 1) narrowband transducer 42 of the linear array to receive a driving pulse from voltage amplifier 124 through 1:20 switch matrix 128. Through control module 125, microprocessor 110 correspondingly instructs voltage pulse amplifier module 124 to prepare an 850 $v_{pp}$, 8.4 microsecond pulse. Because, as noted herein, the system acquires this test data without application of automatic gain control, the system may adjust the pulse amplitude to avoid saturation of the receiving transducer. When amplifier module 124 is ready to transmit, it sends a pulse back to microprocessor 110, and upon receiving an instruction from the microprocessor, provides a high voltage pulse output to the selected transmitting transducer 42. This causes the transmitting transducer to impart a mechanical wave into the concrete sample, causing a resulting p-wave to travel into the concrete and reflect from the opposing side of the concrete or from an intermediate structure or concrete defect. Again, a resonant frequency in the range of 50 KHz is chosen in this example to reduce attenuation effects in concrete, but it should be understood that other frequencies can be utilized, e.g. up to about 120 kHz. Microprocessor 110 sends a signal to control module 136 to select the adjacent (to the right, in FIG. 1) transducer 42 through switch matrix 134, thereby directing the output of the selected receiving transducer to amplifier 118 via relay 116, the state of which the microprocessor selects and controls accordingly. The receiving transducer 42 detects the analog mechanical signal in the concrete and translates the signal to an analog electrical signal that is routed by switch matrix 134 to amplifier module 118 via relay 116. Microprocessor 110 controls amplifier module 118 in this test to amplify, without automatic gain control, the output signal, which is then delivered to analog-to-digital converter 120, where the signal is converted to digital form and saved in SRAM 122. The microprocessor controls the analog to digital converter's sampling rate and number of samples.

Microprocessor 110 then repeats the process, using the previous receiving transducer to transmit and using the next adjacent narrowband transducer 42 to receive. The microprocessor executes the same sequence with respect to this new transducer transmitting/receiving pair. This process repeats for all fourteen transducer pairs in the linear array.

As should be understood, automatic gain control applies a variable gain to incoming signals so that the output amplitude level is within a detecting system's desired signal strength. Automatic gain control is applied to the outputs of the receiving p-wave transducers 40, the receiving s-wave transducers 38, and the broadband transducer 180 (FIG. 7), which do not carry information as amplitude variation. The output from the receiving p-wave transducers 42 do carry information in amplitude, and microprocessor 110 therefore instructs amplifier module 118 to omit automatic gain control from the processing of these signals and adjust the output voltage to avoid saturation. Because the signal from the receiving transducer 42 is acquired without automatic gain control, i.e. with a constant amplification among the receiving transducers in the array, the data received by the application software corresponding to signals detected by this and subsequent receiving transducers in the linear array are comparable to each other, so that the application software can detect the presence of rebar by looking for peaks in the amplitude range of the received signals. More specifically, the microprocessor conveys the data it acquires from memory 122 to the controller unit, which compares the received signal to a predetermined threshold value, and identifies the pressure of rebar if the received signal exceeds the threshold. Alternatively, microprocessor 110 retrieves the signal data from memory 122 and analyzes the signal data for the presence of rebar, reporting to the controller unit the results of that analysis.

The threshold level is determined through testing and calibration, and it accounts for concrete's non-homogeneity. As should be understood, the strength of a signal reflected from rebar will vary inversely to the rebar's depth from the concrete surface, but regardless of depth will generally result in a peak signal as compared to a signal received from the opposing side of the concrete. To calibrate a threshold value, the array of transducers 42 is made to apply a series of signals to a concrete sample known to have rebar. This is repeated for samples having rebar but having different configurations, e.g. different aggregates or curing history, and the threshold set so that a desired percentage of those samples would be identified by application of the threshold. This process is repeated for samples having rebar at differing depths, for instance at one foot or two feet increments, and the threshold possibly adjusted. These thresholds can be programmed at microprocessor 110 or stored in associated memory for its use. Alternatively, rebar depth is assumed only to be at a one foot depth.

In a still further embodiment, the microprocessor collects the output data of all fourteen receiving transducers without analysis, and then upon acquisition of data from all fourteen pairs, uploads the data to the application software at controller unit 20, which in turn determines a respective standard deviation of the peak amplitude values of the signals corresponding to each transducer pair. The application software then determines those transducer pairs having a standard deviation that is significantly different from most of the other transducer pairs and identifies those transducer pairs as having identified rebar. The degree of difference needed to trigger the identification of rebar can be determined through testing against concrete samples known to have rebar. Still further, in another embodiment, the application software determines a standard deviation of the peak amplitude values of the signals for each individual transducer pair, and identifies any transducer pair as having identified rebar if the signal for that transducer pair has a peak value outside a predetermined threshold range beyond the standard deviation.

For each transducer pair for which the application software determines rebar has been identified, regardless of the methodology utilized to make that determination, the application software or microprocessor stores a marker indicating the identity of the receiving transducer at which this occurred.

In a still further embodiment, the control device actuates each individual transducer 42 pair through a sequence of excitation pulses of different amplitude, each therefore resulting in an imparted mechanical wave of different strength, which in turn are capable of traveling and returning (in a detectable strength) to different depths. At each test within the sequence, the microprocessor uploads the resulting data to the controller unit and its application software (although it should be understood this functionality could remain at the microprocessor), and the application software applies the threshold value (directly to amplitude or to a standard deviation analysis) in determining the likelihood of the existence of rebar. If any one of the tests within the sequence for a given transducer pair indicates the likelihood of the presence of rebar, the application software determines that this transducer 42 pair has located the likelihood of the presence of rebar. The process repeats for each other operative transducer 42 pair.

At this point, the application software (or microprocessor 110) has determined, for each pair of transmitting/receiving transducers 42, whether the reflection wave detected by the pair's receiving transducer in response to the pair's transmitting transducer is likely to have reflected from a reinforcing bar within the concrete, based on the peaks as analyzed by controller unit 20 or other criteria. As noted above, LED array 108 includes a plurality of LEDs that are disposed on housing 14 in spatial correspondence to respective transducers 42. That is, the LEDs are arranged in a linear array at a spacing from each other similar to the spacing of the transducer array and in parallel with line 68 (FIG. 1D) so that the individual LEDs are generally aligned with respective transducers 42 in a direction perpendicular to line 68 (FIG. 1D). The correspondence between the individual LEDs and their respective transducers 42 is stored in the programming and/or memory associated with microprocessor 110 and/or the application software. Thus, when the application software (or microprocessor) completes the analysis of the test results from all fourteen transmitter/receiver transducer 42 pairs, the application software sends a signal to the microprocessor, which in turn sends a signal to LED driver 142, via control module 144, causing the LED driver to actuate those LEDs, if any, corresponding to the transmitting transducer in those transducer pairs for which the microprocessor detected rebar. Since this occurs while the user has device 10 pressed up against the concrete surface, the actuated LEDs, if any, provide the user with a visual indication of a concrete surface position above the actual rebar location. In an alternate embodiment, array 108 is replaced by a single LED, and application software/microprocessor 110 actuate this LED whenever any of the transducer 42 pairs indicates the likelihood of rebar.

As noted above, microprocessor 110 communicates with controller unit 20 via a high speed USB controller 138 located on board 100. Upon determining which transmitting transducers in the linear array returned a signal indicating the likelihood of the presence of rebar, controller unit 20 outputs corresponding data to microprocessor 110 via USB 138. That is, having determined (a) the time of flight for the mechanical wave between p-wave transmitting transducer 40c and first p-wave receiving transducer 40a, (b) the time of flight for the mechanical wave between p-wave transmitting transducer 40c and second p-wave receiving transducer 40b, (c) the time of flight for the mechanical wave between s-wave transmitting transducer 38c and first s-wave receiving transducer 38a, and (d) the time of flight for the mechanical wave between s-wave transmitting transducer 38c and second s-wave receiving transducer 38b, and having received from the microprocessor (e) the output from the transmitting/receiving transducer 42 pairs, controller unit 20 (i.e. the application software) calculates p-wave velocity as the difference between the two p-wave flight times, calculates s-wave velocity as the difference between the two s-wave flight times, calculates compressive strength based on the p-wave velocity, the s-wave velocity, and density, determines location (in terms of transducer location) of any identified rebar, and provides the location data to the microprocessor in order for the microprocessor to drive the LED array accordingly.

Figure 10B:
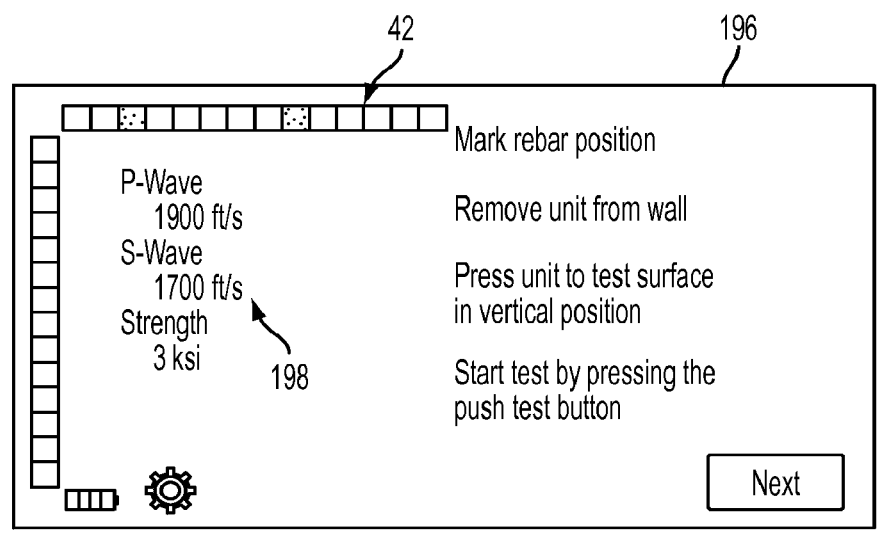

The application software causes the graphical user interface at screen 140 of controller unit 20 in a screen 196 (FIG. 10B) to provide information describing the test results (i.e. p-wave velocity, s-wave velocity, compressive strength, and rebar location) and to provide instructions to the operator to press device 10 to the concrete structure at a position 90 degrees with respect to the first position, and again press a test button 107. Screen 196 provides the previous test results at 198, including identifying (by shading) the positions in the linear array of any transducers 42 whose response data indicated the likelihood of the presence of rebar in the first test.

The user's activation of a "next" button in the display through a touch screen causes the application software to repeat the p-wave velocity test at 160, the s-wave velocity test at 162, the compressive strength calculation at 164, the rebar test at 166, and the LED display of rebar position(s) at 168.

Figure 10C:
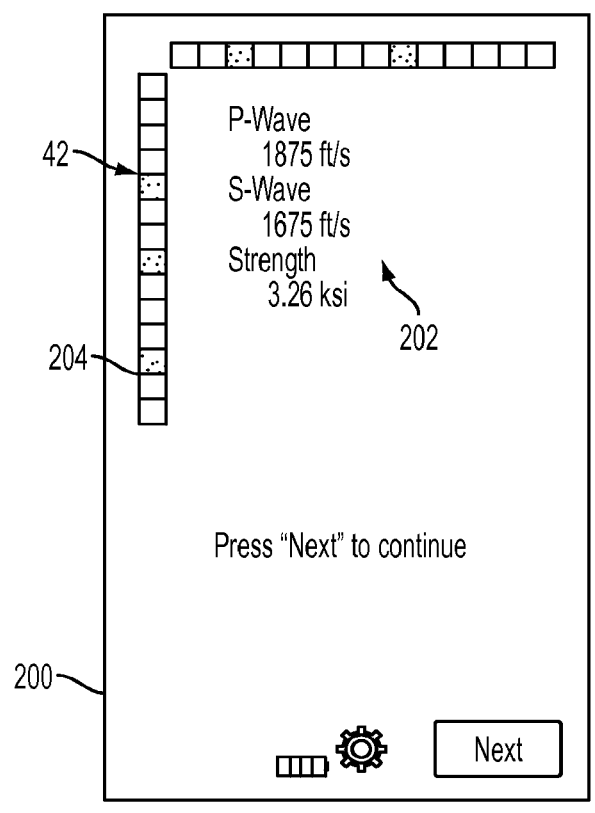
Figure 10D:
Figure 10D:

FIG. 10C illustrates a screen display 200 presented by the graphical user interface at screen 140, at step 170. The test result data presented at 202 is the average of the wave velocities and strength results (although separate identification of the two test results is made in another embodiment) determined at steps 148, 150, 152, 160, 162, and 164. At 204, screen 200 displays (by shading) the positions of those receiving transducers 42 from which data was received indicating likelihood of the presence of rebar in the second test. Screen 140 may be a touch screen, and upon actuation of a "next" button through the touch screen, the graphical user interface presents a screen 206 (FIG. 10D), instructing the user to initiate the thickness test.

In response, the user inserts the data feed line of impact hammer/broadband transducer (with cables) assembly 176 (FIG. 7) into LEMO connector jack 104 of device 10 for execution of the thickness test. Microprocessor 110 detects the insertion over I/O 114, and the microprocessor returns a signal to controller unit 20 confirming that the device is ready for the test. At 172, the application software sends a signal back to microprocessor 110 to initiate the test. In response, microprocessor 110 actuates input selector relay 116 to the state at which relay 116 directs the output of broadband transducer 180 (i.e. the input received at jack 104) to the input of amplifier module 118 but does not acquire output data from transducer 180 until receiving an input signal from impact hammer 178 over input/output 114. The graphical user interface instructions provided at screen 140 (FIG. 2) may instruct the user to strike the concrete with the hammer's steel ball proximate the location at which the broadband transducer is coupled to the concrete surface, i.e. sufficiently close that the resulting mechanical wave imparted to the concrete by the impact hammer creates a standing wave in the concrete sample detectable by the control device through the broadband transducer. In one example, the screen display instructs the server to strike the concrete at a point within fifty mm from the position of broadband transducer 180. Thus, the user now places the acoustic coupling surface of broadband transducer 180 at the surface of concrete sample and, holding the impact hammer, strikes the concrete surface with the steel ball.

The impact hammer produces a mechanical impact on the concrete surface, generating multiple modes of vibration, including p-waves, s-waves, and Rayleigh waves. A piezoelectric element is disposed on the steel ball head that generates an electrical signal when the steel ball strikes the concrete sample. Impact hammer 178 outputs this signal to microprocessor 110, thereby triggering the microprocessor to acquire signal data from broadband transducer 180 that is directed to memory 122.

As should be understood, the resonant frequency of the standing wave created by the hammer impact has a frequency that varies inversely to the concrete sample's thickness. Shallower samples produce higher frequencies, whereas thicker samples produce lower frequencies.

As discussed above, the p-wave creates a standing wave between opposing surfaces of the concrete sample. This wave, and other reflecting waves, excite broadband transducer 180, which converts the mechanical energy into electrical signals that the broadband transducer outputs to amplifier module 118 via relay 116. Amplifier module 118 amplifies, with automatic gain control, the analog signal which is then converted to digital form by analog-to-digital converter 120 and stored in memory 122.

For a six foot concrete sample thickness, the resonant frequency may be in the range of about 1 kHz. In order to detect such a low frequency, the spectral resolution should be decreased, as shown in FIG. 6. For example, if the sampling period of analog to digital converter 120 is twelve microseconds, using a 83.33 kHz clock, and there are 1024 data points (N) in the recorded waveform, the duration of the recorded waveform (N*h) is 12,288 microseconds, which results in a spectral resolution 1/(N*h) of 81 Hz in the signal spectrum. There are 512 frequency channels (N/2), and the maximum sample frequency 1/(2*h) is 42 kHz. The device can display 1,024 samples in the time domain and up to 512 bins (42 k Hz) in the frequency domain. Such a device setup should, therefore, accommodate sample thicknesses at least up to six feet, and it will be understood that accommodation for greater thicknesses can be made through modification of these parameters.

Figure 9:
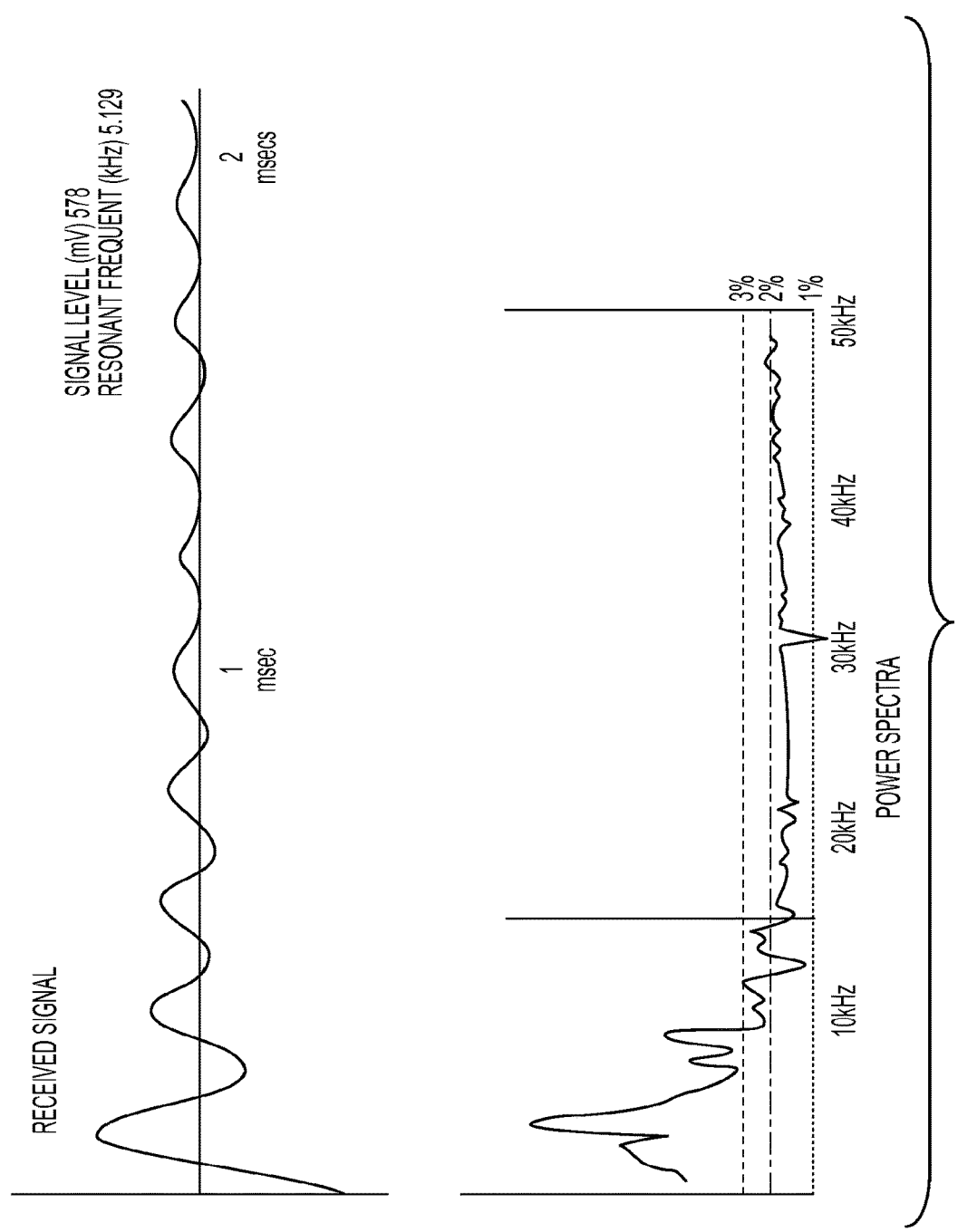
FIG. 9 graphical illustrates a signal generated by a transducer of the device illustrated in FIG. 1A.

Microprocessor 110 acquires the output data from memory 122 and forwards the data to controller unit 20 via USB device 138, and the software application analyzes the data to determine the standing wave's resonant frequency. The software application first sees the data as a time domain waveform (see the upper portion of FIG. 9) but then executes a Fast Fourier transform to convert the time domain signal to a frequency domain signal (as indicated in the lower portion of FIG. 9). The resonant frequency appears as the highest or first (i.e. lowest frequency) peak in this waveform. A Hamming window is used because such method produces less ringing in the spectral values, but it should be understood that other windowing techniques may be employed.

Accordingly, the software application has determined the concrete sample's resonant frequency (f). At 148 and 160, the software application has determined the p-wave velocities in the concrete sample. Averaging the p-wave velocities ($C_p$), the software application, at 174, calculates concrete sample thickness (T) according to the following formula:

$$T = \frac{C_p}{2f}$$

Figure 10E:
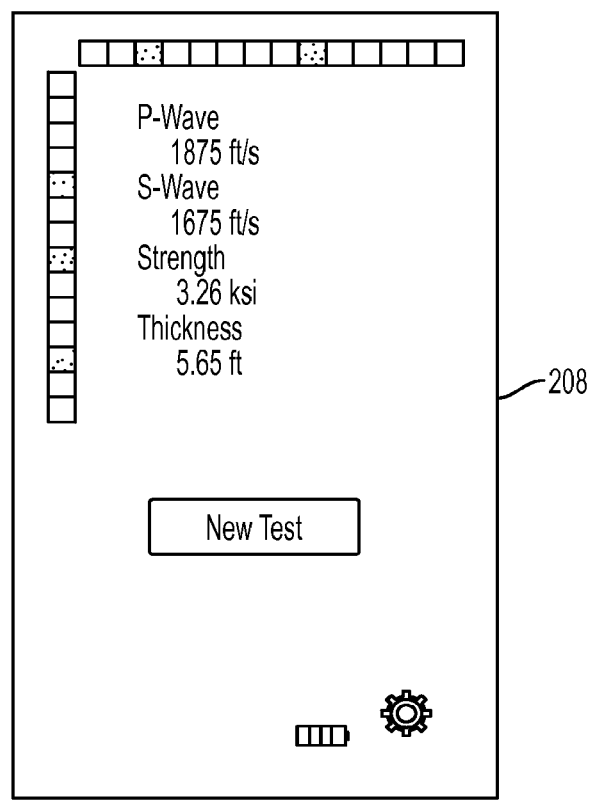

At this point, the testing sequence is complete, and the application software drives the graphical user interface to present a screen 208 (FIG. 10E) at display screen 140 that displays the concrete sample thickness determined by the test.

Because of the non-homogeneity of concrete, the tests described herein may desirably be performed at various positions on the concrete surface.

The software application may act as an intermediary between the user and/or other computers and the basic computer resources of board 100 and controller unit 20, as described, in suitable operating environments. Such software applications include one or both of system and application software. System software can include an operating system, which can be stored on controller device 20 and microprocessor 110, that acts to control and allocate resources of these computer systems. The application software takes advantage of the management resources by system software through program modules and data stored on either or both of system memory and other memory sources, for example mass storage.

Moreover, it will be understood from the present disclosure that the functions ascribed to controller unit 20 and microprocessor 110 may be embodied by computer-executable instructions of a program, for example the application software discussed herein, that runs on one or more computers. Generally, program modules include routines, programs, components, data structures, etc. that perform particular tasks and/or implement particular abstract data types. Moreover, those skilled in the art will appreciate that the systems/methods may be practiced with other computer system configurations, including single-processor, multiprocessor, or multi-core processor computer systems, as well as personal computers and handheld computing devices, microprocessor-based or programmable consumer or industrial electronic, and the like. Aspects of these functions may also be practiced in a distributed computing environment where tasks are performed by remote processing devices that are linked through a communications network. However, some aspects of the claim subject matter can be practiced on stand-alone computers.

Modifications and variations to the particular embodiments of the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to be limitative of the invention so further described in such appended claims.

What is claimed is:

1. A system for determining characteristics of a concrete sample, comprising:
   a concrete sample;
   a frame;
   a plurality of transducers secured by the frame at predetermined positions with respect to each other and so that coupling surfaces of the transducers are generally coplanar with each other; and
   a processor in communication with the transducers and configured to execute computer program instructions to
      actuate a first plurality of the transducers secured by the frame so that the first plurality of transducers impart respective mechanical waves in the concrete sample, and
      receive output signals from a second plurality of the transducers secured by the frame in response to reception of the mechanical waves by the second plurality of transducers,
   wherein the first plurality of transducers are arranged in the frame so that an area
      that is within a plane parallel to the coupling surfaces and in the concrete sample and
      that is bounded within the plane by a collective extent of the respective mechanical waves that pass through the plane and that are receivable by the second plurality of transducers
   has a dimension at least as long as a distance between adjacent reinforcing bars in the concrete sample.

2. The system as in claim 1, wherein the first plurality of transducers and the second plurality of transducers comprise the same transducers.

3. The system as in claim 2, wherein the processor is configured to receive a respective said output signal from each transducer of the second plurality of transducers in response to reception of a said mechanical wave from a different transducer of the first plurality of transducers.

4. The system as in claim 3, wherein the processor is configured to actuate the first plurality of transducers sequentially.

5. The system as in claim 1, wherein the coupling surface of each transducer of the plurality of transducers secured by the frame is circular and has a diameter of about one inch or less.

6. The system as in claim 1, wherein the transducers of the first plurality of transducers are aligned linearly with respect to each other.

7. The system as in claim 6, wherein the coupling surface of each transducer of the plurality of transducers secured by the frame has a center.

8. The system as in claim 7, wherein the centers of each pair of adjacent first transducers are separated by at most about 1.5 inches.

9. The system as in claim 8, wherein the centers of each pair of adjacent first transducers are separated by at most about one inch.

10. The system as in claim 7, wherein the centers of two transducers of the first transducers having the greatest separation between them among the first transducers are separated by at most about 19.5 inches.

11. The system as in claim 8, wherein the centers of two transducers of the first transducers having the greatest separation between them among the first transducers are separated by at most about 19.5 inches.

12. A method for determining characteristics of a concrete sample, comprising:
    providing a frame, and a plurality of transducers secured by the frame at predetermined positions with respect to each other and having respective coupling surfaces;

placing the coupling surfaces on a surface of the concrete sample;

actuating a first plurality of the transducers secured by the frame so that the first plurality of transducers impart respective mechanical waves in the concrete sample; and receiving output signals from a second plurality of the transducers secured by the frame in response to reception of the mechanical waves by the second plurality of transducers, wherein the first plurality of transducers are arranged in the frame so that an area that is within a plane offset from the coupling surfaces and in the concrete sample and that is bounded within the plane by a collective extent of the respective mechanical waves that pass through the plane and that are receivable by the second plurality of transducers has a dimension at least as long as a distance between adjacent reinforcing bars in the concrete sample.

13. The method as in claim 12, wherein the first plurality of transducers and the second plurality of transducers comprise the same transducers.

14. The method as in claim 13, wherein the receiving step comprises receiving a respective said output signal from each transducer of the second plurality of transducers in response to reception of a said mechanical wave from a different transducer of the first plurality of transducers.

15. The method as in claim 14, wherein the actuating step comprises actuating the first plurality of transducers sequentially.

16. The method as in claim 12, wherein the transducers of the first plurality of transducers are aligned linearly with respect to each other.

17. The method as in claim 16, wherein the coupling surface of each transducer of the plurality of transducers secured by the frame has a center.

18. The method as in claim 17, wherein the centers of each pair of adjacent first transducers are separated by at most a distance equal to about one-half of a minimum separation between adjacent reinforcing bars in the concrete sample.

19. The method as in claim 18, wherein the centers of each pair of adjacent first transducers are separated by at most about 1.5 inches.

20. The method as in claim 17, wherein the centers of two transducers of the first transducers having the greatest separation between them among the first transducers are separated by at most about 19.5 inches.

21. The method as in claim 19, wherein the centers of two transducers of the first transducers having the greatest separation between them among the first transducers are separated by at most about 19.5 inches.

22. The method as in claim 12, wherein the distance corresponds to a maximum separation between adjacent reinforcing bars in the concrete sample.

* * * * *